United States Patent
Nezu et al.

(10) Patent No.: US 7,022,474 B2
(45) Date of Patent: Apr. 4, 2006

(54) FETALLY EXPRESSED GENE AS A HUMAN COLON CANCER MARKER

(75) Inventors: Jun-Ichi Nezu, Ibaraki (JP); Asuka Ose, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 382 days.

(21) Appl. No.: 09/974,143

(22) Filed: Oct. 9, 2001

(65) Prior Publication Data

US 2003/0022326 A1 Jan. 30, 2003

Related U.S. Application Data

(63) Continuation-in-part of application No. PCT/JP00/02281, filed on Apr. 7, 2000.

(30) Foreign Application Priority Data

Apr. 9, 1999 (JP) .......................................... 11-103356

(51) Int. Cl.
*C12Q 1/68* (2006.01)

(52) U.S. Cl. ........................ 435/6; 435/69.1; 435/320.1; 435/252.3; 435/254.11; 435/419; 435/325; 536/23.1; 536/23.5

(58) Field of Classification Search ................ 536/23.1, 536/23.5; 435/320.1, 252.3, 254.11, 325, 435/419, 69.1, 6
See application file for complete search history.

(56) References Cited

U.S. PATENT DOCUMENTS

2002/0115599 A1 * 8/2002 Vernos et al. .................. 514/12

FOREIGN PATENT DOCUMENTS

| WO | WO 99/04265 | * 1/1999 |
|---|---|---|
| WO | WO 99/37788 | 7/1999 |
| WO | WO 00/60071 | 10/2000 |
| WO | WO 01/57058 | 8/2001 |

OTHER PUBLICATIONS

Ambrosini G et al, Nat Med, 1997, 3(8);917–21.
Su L, et al., Genes Dev, 1993, 7(5);735–48.
Bischoff et al., "A homologue of Drosophilia aurora kinase is oncogenic and amplified in human colorectal cancers", *The EMBO Journal*, vol. 17 No. 11 pp. 3052–3065, 1998.
Fram et al., "Immunoenzymatic detection of the new proliferation associated protein p100 by means of a cellular ELISA: specific detection of cells in cell cycle phases S, G2 and M", *Journal of Immunological Methods*, 233 pp. 147–153, 1999.
Nezu, J., "Fetal gene preferentially expressed in colorectal cancer", *Database EMBL Online!*, Database accession No. AB024704, Apr. 20, 1999.
Tamai et al., "Cloning and characterization of a novel human pH–dependent organic cation transporter, OCTN1", *FEBS Letters*, 419 pp107–111, 1997.
Hufton et al., 1999, FEBS Letters, vol. 463;77–82.
Manda et al., 1999, Genomics, vol. 62;5–14.
Wittmann et al., 2000, J.Cell.Biol., vol. 149, No. 7;1405–1418.
Zhang et al., 1999, Cytogenet Cell Genet, vol. 84; 182–183.

\* cited by examiner

*Primary Examiner*—Kathleen Kerr
(74) *Attorney, Agent, or Firm*—Fish & Richardson P.C.

(57) ABSTRACT

Novel fetal genes (fls353 and fls485) have been successfully isolated from human fetal liver-derived cDNAs. These genes were specifically expressed in tissues including fetal tissues which are thought to contain a large number of undifferentiated cells and actively differentiating/proliferating cells. High levels of expression of these genes were observed also in a variety of cancer cells. The proteins and genes encoding the proteins can be used as the tool for developing drugs for the treatment of tumors.

21 Claims, 11 Drawing Sheets

```
   1 CAGGTCTGAGGCGAAGCTAGGTGAGCCGTGGGAAGAAAAGAGGGAGCAGCTAGGGCGCGG    60
  61 GTCTCCCTCCTCCCGGAGTTTGGAACGGCTGAAGTTCACCTTCCAGCCCCTAGCGCCGTT   120
 121 CGCGCCGCTAGGCCTGGCTTCTGAGGCGGTTGCGGTGCTCGGTCGCCGCCTAAGCGGGGC   180
 181 AGGGTGCGAACAGGGGCTTCGGGCCACGCTTCTCTTGGCGACAGGATTTTGCTGTGAAGT   240
 241 CCGTCCGGGAAACGGAGGAAAAAAAGAGTTGCGGGAGGCTGTCTGCTAATAACGGTTCTT   300
 301 GATACATATTTGCCAGACTTCAAGATTTCAGAAAAGGGGTGAAAGAGAAGATTGCAACTT   360
 361 TGAGTCAGACCTGTAGGCCTGATAGACTGATTAAACCACAGAAGGTGACCTGCTGAGAAA   420
 421 AGTGGTACAAATACTGGGAAAAACCTGCTCTTCTGCGTTAAGTGGGAGACAATGTCACAA   480
   1                                                            M  S  Q    3
 481 GTTAAAAGCTCTTATTCCTATGATGCCCCCTCGGATTTCATCAATTTTTCATCCTTGGAT   540
   4  V  K  S  S  Y  S  Y  D  A  P  S  D  F  I  N  F  S  S  L  D   23
 541 GATGAAGGAGATACTCAAAACATAGATTCATGGTTTGAGGAGAAGGCCAATTTGGAGAAT   600
  24  D  E  G  D  T  Q  N  I  D  S  W  F  E  E  K  A  N  L  E  N   43
 601 AAGTTACTGGGGAAGAATGGAACTGGAGGGCTTTTTCAGGGCAAAACTCCTTTGAGAAAG   660
  44  K  L  L  G  K  N  G  T │G  G  L  F  Q  G  K  T│ P  L  R  K    63
 661 GCTAATCTTCAGCAAGCTATTGTCACACCTTTGAAACCAGTTGACAACACTTACTACAAA   720
  64  A  N  L  Q  Q  A  I  V  T  P  L  K  P  V  D  N  T  Y  Y  K   83
 721 GAGGCAGAAAAAGAAAATCTTGTGGAACAATCCATTCCGTCAAATGCTTGTTCTTCCCTG   780
  84  E  A  E  K  E  N  L  V  E  Q  S  I  P  S  N  A  C  S  S  L  103
 781 GAAGTTGAGGCAGCCATATCAAGAAAAACTCCAGCCCAGCCTCAGAGAAGATCTCTTAGG   840
 104  E  V  E  A  A  I  S  R  K  T  P  A  Q  P  Q  R  R  S  L  R  123
 841 CTTTCTGCTCAGAAGGATTTGGAACAGAAAGAAAAGCATCATGTAAAAATGAAAGCCAAG   900
 124  L  S  A  Q  K  D  L  E  Q  K  E  K  H  H  V  K  M  K  A  K  143
 901 AGATGTGCCACTCCTGTAATCATCGATGAAATTCTACCCTCTAAGAAAATGAAAGTTTCT   960
 144  R  C  A  T  P  V  I  I  D  E  I  L  P  S  K  K  M  K  V  S  163
 961 AACAACAAAAAGAAGCCAGAGGAAGAAGGCAGTGCTCATCAAGATACTGCTGAAAACAAT  1020
 164  N  N  K  K  K  P  E  E  E  G  S  A  H  Q  D  T  A  E  N  N  183
1021 GCATCTTCCCCAGAGAAAGCCAAGGGTAGACATACTGTGCCTTGTATGCCACCTGCAAAG  1080
 184  A  S  S  P  E  K  A  K  G  R  H  T  V  P  C  M  P  P  A  K  203
1081 CAGAAGTTTCTAAAAAGTACTGAGGAGCAAGAGCTGGAGAAGAGTATGAAAATGCAGCAA  1140
 204  Q  K  F  L  K  S  T  E  E  Q  E  L  E  K  S  M  K  M  Q  Q  223
1141 GAGGTGGTGGAGATGCGGAAAAAGAATGAAGAATTCAAGAAACTTGCTCTGGCTGGAATA  1200
 224  E  V  V  E  M  R  K  K  N  E  E  F  K  K  L  A  L  A  G  I  243
1201 GGGCAACCTGTGAAGAAATCAGTGAGCCAGGTCACCAAATCAGTTGACTTCCACTTCCGC  1260
 244  G  Q  P  V  K  K  S  V  S  Q  V  T  K  S  V  D  F  H  F  R  263
1261 ACAGATGAGCGAATCAAACAACATCCTAAGAACCAGGAGGAATATAAGGAAGTGAACTTT  1320
 264  T  D  E  R  I  K  Q  H  P  K  N  Q  E  E  Y  K  E  V  N  F  283
1321 ACATCTGAACTACGAAAGCATCCTTCATCTCCTGCCCGAGTGACTAAGGGATGTACCATT  1380
 284  T  S  E  L  R  K  H  P  S  S  P  A  R  V  T  K  G  C  T  I  303
1381 GTTAAGCCTTTCAACCTGTCCCAAGGAAAGAAAAGAACATTTGATGAAACAGTTTCTACA  1440
 304  V  K  P  F  N  L  S  Q  G  K  K  R  T  F  D  E  T  V  S  T  323
1441 TATGTGCCCCTTGCACAGCAAGTTGAAGACTTCCATAAACGAACCCCTAACAGATATCAT  1500
 324  Y  V  P  L  A  Q  Q  V  E  D  F  H  K  R  T  P  N  R  Y  H  343
1501 TTGAGGAGCAAGAAGGATGATATTAACCTGTTACCCTCCAAATCTTCTGTGACCAAGATT  1560
 344  L  R  S  K  K  D  D  I  N  L  L  P  S  K  S  S  V  T  K  I  363
1561 TGCAGAGACCCACAGACTCCTGTACTGCAAACCAAACACCGTGCACGGGCTGTGACCTGC  1620
 364  C  R  D  P  Q  T  P  V  L  Q  T  K  H  R  A  R  A  V  T  C  383
1621 AAAAGTACAGCAGAGCTGGAGGCTGAGGAGCTCGAGAAATTGCAACAATACAAATTCAAA  1680
 384  K  S  T  A  E  L  E  A  E  E  L  E  K  L  Q  Q  Y  K  F  K  403
1681 GCACGTGAACTTGATCCAGAATACTTGAAGGTGGGCCCATCTTGCCCAAGAAACCACCT  1740
 404  A  R  E  L  D  P  R  I  L  E  G  G  P  I  L  P  K  K  P  P  423
```

FIG. 4

```
1741 GTGAAACCACCCACCGAGCCTATTGGCTTTGATTTGGAAATTGAGAAAAGAATCCAGGAG   1800
 424  V  K  P  P  T  E  P  I  G  F  D  L  E  I  E  K  R  I  Q  E    443

1801 CGAGAATCAAAGAAGAAAACAGAGGATGAACACTTTGAATTTCATTCCAGACCTTGCCCT   1860
 444  R  E  S  K  K  K  T  E  D  E  H  F  E  F  H  S  R  P  C  P    463

1861 ACTAAGATTTTGGAAGATGTTGTGGGTGTTCCTGAAAAGAAGGTACTTCCAATCACCGTC   1920
 464  T  K  I  L  E  D  V  V  G  V  P  E  K  K  V  L  P  I  T  V    483

1921 CCCAAGTCACCAGCCTTTGCATTGAAGAACAGAATTCGAATGCCCACCAAAGAAGATGAG   1980
 484  P  K  S  P  A  F  A  L  K  N  R  I  R  M  P  T  K  E  D  E    503

1981 GAAGAGGACGAACCGGTAGTGATAAAAGCTCAACCTGTGCCACATTATGGGGTGCCTTTT   2040
 504  E  E  D  E  P  V  V  I  K  A  Q  P  V  P  H  Y  G  V  P  F    523

2041 AAGCCCCAAATCCCAGAGGCAAGAACTGTGGAAATATGCCCTTTCTCGTTTGATTCTCGA   2100
 524  K  P  Q  I  P  E  A  R  T  V  E  I  C  P  F  S  F  D  S  R    543

2101 GACAAAGAACGTCAGTTACAGAAGGAGAAGAAAATAAAAGAACTGCAGAAAGGGGAGGTG   2160
 544  D  K  E  R  Q  L  Q  K  E  K  K  I  K  E  L  Q  K  G  E  V    563

2161 CCCAAGTTCAAGGCACTTCCCTTGCCTCATTTTGACACCATTAACCTGCCAGAGAAGAAG   2220
 564  P  K  F  K  A  L  P  L  P  H  F  D  T  I  N  L  P  E  K  K    583

2221 GTAAAGAATGTGACCCAGATTGAACCTTTCTGCTTGGAGACTGACAGAAGAGGTGCTCTG   2280
 584  V  K  N  V  T  Q  I  E  P  F  C  L  E  T  D  R  R  G  A  L    603

2281 AAGGCACAGACTTGGAAGCACCAGCTGGAAGAAGAACTGAGACAGCAGAAAGAAGCAGCT   2340
 604  K  A  Q  T  W  K  H  Q  L  E  E  E  L  R  Q  Q  K  E  A  A    623

2341 TGTTTCAAGGCTCGTCCAAACACCGTCATCTCTCAGGAGCCCTTTGTTCCCAAGAAAGAG   2400
 624  C  F  K  A  R  P  N  T  V  I  S  Q  E  P  F  V  P  K  K  E    643

2401 AAGAAATCAGTTGCTGAGGGCCTTTCTGGTTCTCTAGTTCAGGAACCTTTTCAGCTGGCT   2460
 644  K  K  S  V  A  E  G  L  S  G  S  L  V  Q  E  P  F  Q  L  A    663

2461 ACTGAGAAGAGAGCCAAAGAGCGGCAGGAGCTGGAGAAGAGAATGGCTGAGGTAGAAGCC   2520
 664  T  E  K  R  A  K  E  R  Q  E  L  E  K  R  H  A  E  V  E  A    683

2521 CAGAAAGCCCAGCAGTTGGAGGAGGCCAGACTACAGGAGGAAGAGCAGAAAAAAGAGGAG   2580
 684  Q  K  A  Q  Q  L  E  E  A  R  L  Q  E  E  E  Q  K  K  E  E    703

2581 CTGGCCAGGCTACGGAGAGAACTGGTGCATAAGGCAAATCCAATACGCAAGTACCAGGGT   2640
 704  L  A  R  L  R  R  E  L  V  H  K  A  N  P  I  R  K  Y  Q  G    723

2641 CTGGAGATAAAGTCAAGTGACCAGCCTCTGACTGTGCCTGTATCTCCCAAATTCTCCACT   2700
 724  L  E  I  K  S  S  D  Q  P  L  T  V  P  V  S  P  K  F  S  T    743

2701 CGATTCCACTGCTAAACTCAGCTGTGAGCTGCGGATACCGCCCGGCAATGGGACCTGCTC   2760
 744  R  F  H  C                                                     747

2761 TTAACCTCAAACCTAGGACCGTCTTGCTTTGTCATTGGGCATGGAGAGAACCCATTTCTC   2820

2821 CAGACTTTTACCTACCCGTGCCTGAGAAAGCATACTTGACAACTGTGGACTCCAGTTTTG   2880

2881 TTGAGAATTGTTTTCTTACATTACTAAGGCTAATAATGAGATGTAACTCATGAATGTCTC   2940

2941 GATTAGACTCCATGTAGTTACTTCCTTTAAACCATCAGCCGGCCTTTTATATGGGTCTTC   3000

3001 ACTCTGACTAGAATTTAGTCTCTGTGTCAGCACAGTGTAATCTCTATTGCTATTGCCCCT   3060

3061 TACGACTCTCACCCTCTCCCCACTTTTTTTAAAAATTTTAACCAGAAAATAAAGATAGTT   3120

3121 AAATCCTAAGATAGAGATTAAGTCATGGTTTAAATGAGGAACAATCAGTAAATCAGATTC   3180

3181 TGTCCTCTTCTCTGCATACCGTGAATTTATAGTTAAGGATCCCTTTGCTGTGAGGGTAGA   3240

3241 AAACCTCACCAACTGCACCAGTGAGGAAGAAGACTGCGTGGATTCATGGGGAGCCTCACA   3300

3301 GCAGCCACGCAGCAGGCTCTGGGTGGGGCTGCCGTTAAGGCACAGTTCTTTCCTTACTGG   3360

3361 TGCTGATAACAACAGGGAACCGTGCAGTGTGCATTTTAAGACC                    3403
```

FIG. 5

```
  1 CTCACACTGGCTGGCACTGCTAAGCAGGTGCGGAGGGGAGTCAGAGACCCCCGGATGGAG      60
 61 GGGTGTGGTGGACCTCAGTTTTGAGGCCGAGAGTCCTCTGGCGCCCCCCACAGAGCTCCT     120
121 GGAGAGACTGCCCAGCTATGACTGGCTTCTTCAAGGGGGCAGAGGACAGATATTCTTCCC     180
181 ACCTTTGGAGGCCCCAGGGAGGCCCCAGGAGCAAAGGTCCTGGCCCTCGTTCCTGGAACA     240
241 CAGGAGATGCCCTCCCCAGTTGGACTGCTGAGGGCTTTACCACTACCGTGGCCTCAGTTT     300
  1      M  P  S  P  V  G  L  L  R  A  L  P  L  P  W  P  Q  F       18
301 CTCGCCTGCACGTTGAGGAGGCTGGCTGGCCCGCGTGAGTCCACAGGCCCTTCCCAGAAG     360
 19  L  A  C  T  L  R  R  L  A  G  P  R  E  S  T  G  P  S  Q  K    38
361 CCCCCGCCTCTCTGTTCGGTCCCCTGCAGAGTCCCTGCGATGACGGAGGAGGTGGCCCGG     420
 39  P  P  P  L  C  S  V  P  C  R  V  P  A (M) T  E  E  V  A  R    58
421 GAAGCCCTCCTCAGCTTTGTGGACTCTAAGTGCTGCTACAGCAGCACGGTGGCTGGAGAC     480
 59  E  A  L  L  S  F  V  D  S  K  C  C  Y  S  S  T  V  A  G  D    78
481 CTCGTCATCCAGGAGCTGAAGCGGCAGACCCTCTGCAGGTACCGTCTGGAGACCTTTAGT     540
 79  L  V  I  Q  E  L  K  R  Q  T  L  C  R  Y  R  L  E  T  F  S    98
541 GAATCCAGGATAAGCGAGTGGACATTTCAACCCTTTACTAACCACTCTGTGGATGGGCCG     600
 99  E  S  R  I  S  E  W  T  F  Q  P  F  T  N  H  S  V  D  G  P   118
601 CAAAGAGGCGCCTCCCCCAGGCTCTGGGACATCAAGGTTCAAGGTCCTCCGATGTTTCAG     660
119  Q  R  G  A  S  P  R  L  W  D  I  K  V  Q  G  P  P  M  F  Q   138
661 GAAGACACCAGGAAGTTCCAGGTCCCTCACTCGTCACTGGTCAAGGAATGCCACAAATGC     720
139  E  D  T  R  K  F  Q  V  P  H  S  S  L  V  K  E [C  H  K  C   158
721 CATGGGCGTGGGCGGTACAAGTGCAGCGGCTGCCACGGGGCGGGCACGGTGCGGTGCCCA     780
159  H  G  R  G] R  Y  K [C  S  G  C  H  G  A  G] T  V  R [C  P   178
781 TCCTGCTGCGGAGCCAAGCGCAAAGCCAAGCAGTCCCGGAGATGTCAGCTGTGCGCGGGG     840
179  S  C  C  G] A  K  R  K  A  K  Q  S  R  R [C  Q  L  C  A  G   198
841 TCCGGCAGGCGAAGATGCAGCACTTGCTCAGGGAGAGGGAACAAGACCTGCGCCACCTGC     900
199  S  G] R  R  R [C  S  T  C  S  G  R  G] N  K  T [C  A  T  C   218
901 AAGGGGGAGAAGAAGCTGTTGCACTTCATCCAGCTTGTCATCATGTGGAAGAACAGCTTG     960
219  K  G] E  K  K  L  L  H  F  I  Q  L  V  I  M  W  K  N  S  L   238
961 TTTGAGTTTGTGTCTGAGCACCGGCTCAACTGCCCCAGGGAGCTTCCTTGCTAAAGCCAAA    1020
239  F  E  F  V  S  E  H  R  L  N  C  P  R  E  L  L  A  K  A  K   258
1021 GGAGAAAACCTCTTTAAGGATGAAAACTCGGTGGTGTACCCCATCGTGGACTTCCCTCTG    1080
259  G  E  N  L  F  K  D  E  N  S  V  V  Y  P  I  V  D  F  P  L   278
1081 CGAGACATCTCTCTTGCCTCCCAGAGGGGCATTGCAGAGCACAGCGCTGCCTTGGCCTCC    1140
279  R  D  I  S  L  A  S  Q  R  G  I  A  E  H  S  A  A  L  A  S   298
1141 CGTGCCCGCGTCCTGCAGCAGCGCCAGACCATTGAGCTGATCCCCCTCACAGAAGTTCAC    1200
299  R  A  R  V  L  Q  Q  R  Q  T  I  E  L  I  P  L  T  E  V  H   318
1201 TATTGGTACCAAGGAAAGACTTATGTCTACTACATCTATGGCACTGACCACCAGGTGTAT    1260
319  Y  W  Y  Q  G  K  T  Y  V  Y  Y  I  Y  G  T  D  H  Q  V  Y   338
1261 GCGGTGGACTATCCTGAGCGGTATTGCTGTGGCTGTACCATCGTGTGACATAGCATGGCT    1320
339  A  V  D  Y  P  E  R  Y  C  C  G  C  T  I  V  *               353
1321 GTCCCCAGAGCCTGCCATTCACGTTTGCCAAGGAAGATGGCCGACACTCTCTGAGTGTGT    1380
1381 TCACTGTTGGCTGCATTGGACAATCACATACAAACCCTCGGCATGTCCTTCCAGAAAAACC    1440
1441 AGCTTATCATCTATCAAGCTCCAACCCCTTATACAGCTCCTCTGGTGGAATCCATGACTC    1500
1501 ATATGTTTAACCTACAATAATTCAGCTATACCCATTCCTGTAAAA                   1545
```

FIG. 8

FETALLY EXPRESSED GENE AS A HUMAN COLON CANCER MARKER

This application is a continuation-in-part of PCT/JP00/02281, filed Apr. 7, 2000, and claims priority from Japanese Patent Application No. 11/103356, filed Apr. 9, 1999.

TECHNICAL FIELD

The present invention relates to proteins encoded by fetal genes the expression of which is activated in fetal tissues and tumor cells. Proteins of this invention can be utilized as target molecules for developing medicines for the treatment of cancer.

BACKGROUND

Fetal tissues are comprised of many undifferentiated cells that proliferate actively, highly activated cells, nascent vascular endothelial cells, and so on. Although these are stringently regulated in fetal tissues and inhibited as individuals mature, this can be considered very similar to the state of a solid tumor except that the activity is regulated. Therefore, some of the genes expressed specifically in fetal tissues (fetal genes) can be genes involved in the phenomena characteristic of solid tumors such as abnormal growth, immortalization, infiltration, metastasis, and angiogenesis. In addition, some diseases other than cancers are also supposed to arise because fetal genes, which are repressed in a normal living body, are abnormally activated. Therefore, genes involved in various diseases such as cancers can be screened by isolating and analyzing fetal genes. Furthermore, development of medicines using novel action mechanisms is thought to be possible by designing drugs targeted on the genes.

Recently, as fetal genes which are assumed to be involved in malignant transformation, genes for survivin (Nat. Med., 3:917–921, 30 1997), aurora kinase (EMBO J., 17:3052–3065, 1998) and LYAR (Genes Dev., 7:735–748, 1993) have been reported. Their expressions are all activated in colon cancer, leukemia cells, and such, and these genes are thought to contribution importantly to the malignant transformation. In fact, it has been demonstrated that survivin has the apoptosis inhibitor activity, and aurora kinase participates in the cell cycle regulation as their physiological functions, indicating that acquiring function of either of them works favorably for cancer cells.

SUMMARY

The present invention provides novel proteins specifically or more strongly expressed in fetal tissues, genes encoding the proteins, and preparation and uses of them.

As a method for isolating a gene involved in the malignant transformation, many strategies have been hither to tried where cancer cells and normal cells are directly compared so as to identify a common gene the expression level of which is significantly different. However, such a method had a problem that a large number of genes not directly in involved in malignant transformation might be isolated as the noise due to irregularity in the gene expression control, which is one of characteristics of cancer cells, leading to no isolation of important genes. Therefore, the present inventors have planned a strategy where genes, the expression of which is physiologically controlled from physiological necessity, are first selected and examined whether the genes are abnormally reactivated under non-physiological conditions such as cancer. Based on this strategy, the inventors have focused on the genes specifically expressed in fetal tissues as the genes the expression of which is physiologically controlled from the physiological necessity, and performed their isolations and analyses.

Specifically, first, by the suppression subtractive hybridization method, the present inventors performed the subtraction method with cDNA derived from fetal liver as the tester and cDNA derived from adult liver as the driver to search for fetal genes expressed specifically or more strongly in the fetal liver.

As a result, they isolated a plurality of genes. Then, they examined these genes specifically expressed in fetal tissues for their expression levels in cancer cells. As a result, they have succeeded in identifying novel genes, "fls353" and "fls485" the expressions of which are activated in cancer cells such as colon cancer and hepatoma and so on. Cloning of these full-length cDNAs followed by their sequencings have revealed that, although amino acid sequences of proteins encoded by these genes comprise several characteristic domain structures, no protein having a particularly significant homology to these gene products could be detected in the database. As a result of further studies on the tissue specificities of these gene expressions in more detail, the present inventors have found that these genes are expressed in a variety of cancer cells, and also specifically in normal tissues, such as fetal tissues and other tissues which are thought to contain many undifferentiated cells and actively differentiating/proliferating cells.

These facts have strongly suggested participation of the novel fetal genes "fls353" and "fls485" in the malignant transformation of cells. Therefore, not only expression inhibitors of these fetal genes are expected to be used as the anticancer agent but also fetal genes and proteins encoded by the genes according to this invention can be used as the tool for developing drugs for the treatment of cancer.

The present invention relates to the novel fetal genes "fls353" and "fls485" which are presumed to be involved in the malignant transformation, and the proteins encoded by these genes as well as their preparations and uses, and more specifically, this invention is to provide the following:

(1) A DNA of any one of (a) to (d) below:
 (a) a DNA encoding a protein comprising the amino acid sequence of any one of SEQ ID NOs:2, 4 and 6,
 (b) a DNA comprising a coding region in the nucleotide sequence of any one of SEQ ID NOs:1, 3 and 5,
 (c) a DNA encoding a protein that comprises the amino acid sequence of any one of SEQ ID NOs:2, 4 and 6 in which one or more amino acids are replaced, deleted, inserted and/or added and that is functionally equivalent to the protein comprising the amino acid sequence of any one of SEQ ID NOs:2, 4 and 6, and
 (d) a DNA that hybridizes under stringent conditions with the DNA comprising the nucleotide sequence of any one of SEQ ID NOs:1, 3 and 5 and that codes a protein functionally equivalent to the protein comprising the amino acid sequence of any one of SEQ ID NOs:2, 4 and 6.

(2) A DNA encoding a partial peptide of a protein comprising the amino acid sequence of any one of SEQ ID NOs:2, 4 and 6.

(3) A vector into which the DNA of (1) or (2) is inserted.

(4) A transformant harboring the DNA of (1) or (2) or the vector of (3).

(5) A protein or a peptide encoded by the DNA of (1) or (2).

(6) A method for producing the protein or the peptide of (5), the method comprising the steps of culturing the transformant of (4) and recovering a protein expressed from the transformant or the culture supernatant thereof.

(7) An antibody against the protein of (5).

(8) A polynuclelotide that hybridizes with the DNA comprising the nucleotide sequence of any one of SEQ ID NOs:1, 3 and 5 or the complementary strand thereof and that comprises at least 15 nucleotides.

(9) A method for screening a compound binding to the protein of (5), the method comprising the steps of:
(a) contacting a test sample with the protein or a partial peptide thereof,
(b) detecting a binding activity of the test sample to the protein or the partial peptide thereof, and
(c) selecting a compound comprising the biding activity to the protein or the partial peptide thereof.

(10) A compound biding to the protein of (5), wherein the compound can be isolated by the method of (9).

(11) A method for screening a compound that suppresses or promotes expression of the DNA of (1), wherein the method comprises the steps of:
(a) contacting a test sample with cells expressing the DNA,
(b) detecting the expression of the DNA in the cells, and
(c) selecting a compound that decreases or increases the expression of the DNA compared with that in the case where the test sample is not contacted with the cells (control).

(12) A method for screening a compound that suppresses or promotes expression of the DNA of (1), wherein the method comprises the steps of:
(a) providing cells into which a vector comprising a reporter gene functionally linked downstream of the expression control region of the DNA of (1),
(b) contacting a test sample with the cells,
(c) detecting the activity of the reporter gene in the cells, and
(d) selecting a compound that decreases or increases the activity compared with that in the case where the test sample is not contacted with the cells (control).

(13) A compound that suppresses or promotes expression of the DNA of (1), wherein the compound can be isolated by the method of (11) or (12).

BRIEF DESCRIPTION OF THE DRAWINGS

FIG. 4 shows the nucleotide sequence of fls353 and its putative amino acid sequence (SEQ ID NOs:1 and 2 respectively. Amino acids corresponding to the consensus sequence at the ATP/GTP binding site are shown enclosed by a solid line. Continued to FIG. 5.

FIG. 5 is the continuation of FIG. 4.

FIG. 8 shows the nucleotide sequence of fls485 L (SEQ ID NO:3) and its putative amino acid sequence (SEQ ID NO:4). Fls485 S has the same sequence as fls485 L except that in fls485 S, the domain underlined in FIG. 8 does not exist, and the encircled methionine (M) is assumed to be used as the initiation codon. The nucleotide and amino acid sequences of fls485 S are shown in SEQ ID NOs: 5 and 6, respectively. Sequence surrounded by the solid square is the amino acid sequence coinciding with the sequence comprising Cys-Xaa-Xaa-Cys-Xaa-Gly-Xaa-Gly, and that surrounded by the dotted square is the amino acid sequence coinciding with the sequence comprising Cys-Xaa-Xaa-Cys-Xaa-Gly.

Figure 1:
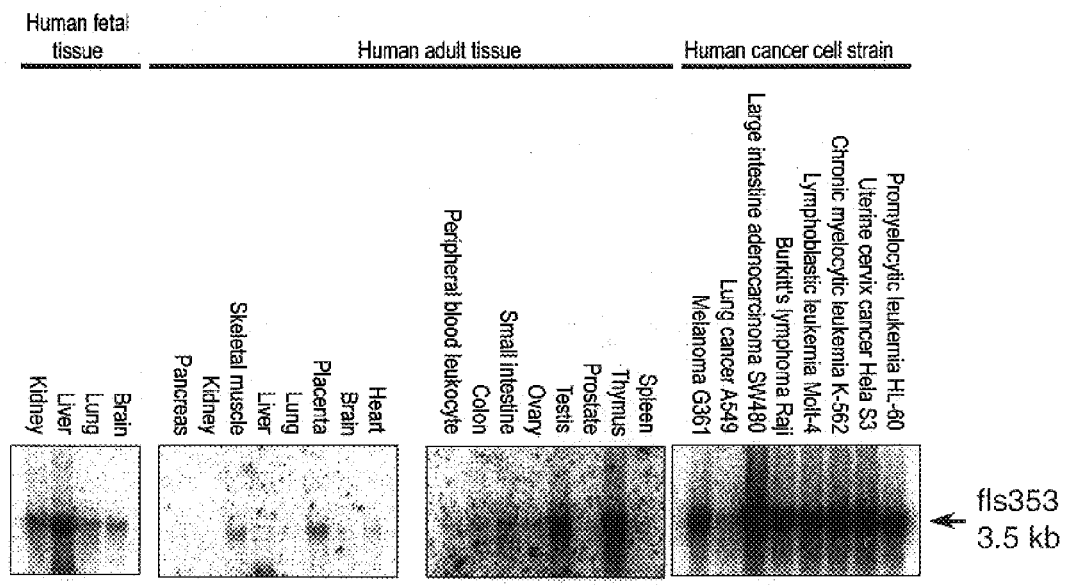
FIG. 1 is a photograph showing the results of the fls353 expression examined by northern analysis.

This invention relates to the novel proteins "fls353" and "fls485" the expressions of which are activated in fetal tissues and tumor cells. Nucleotide sequence of cDNA for the novel human fetal gene "fls353" is set forth in SEQ ID NO:1, and two types of nucleotide sequences of cDNAs for the novel human fetal gene "fls485" which are included in this invention are set forth in SEQ ID NO:3 (fls485 L) and 5 (fls485 S), respectively. Amino acid sequences encoded by these cDNAs are set forth in SEQ ID NO:2 (fls353), 4 (fls485 L) and 6 (fls485 S), respectively.

In normal tissues, those genes have been found to be specifically expressed in undifferentiated cells such as in fetal tissues, and in tissues which are thought to contain many actively differentiating and proliferating cells. Examination of their expressions in cancer cells revealed that they were activated in those such as colon cancer and hepatoma and so on.

As to fetal genes, genes for survivin, aurora kinase and LYAR have been assumed to be involved in malignant transformation, and it has been reported that expressions of the genes show a common pattern that their expressions in normal tissues are prominent in fetal tissues, especially in the fetal liver, and that in adult tissues their expressions are abundant in tissues such as testis and thymus containing many actively proliferating undifferentiated cells but not detected in other tissues than those at all (Nat. Med., 3:917–921, 1997; EMBO J., 17:3052–3065, 1998; and Genes Dev., 7:735–748, 1993). This common expression pattern is shared by nearly all of fetal genes in this invention, indicating that such a common feature may be produced from the necessity for cell proliferation.

Although mechanisms by which cancer cells reactivate such genes favorably acting for their own proliferation have not been elucidated, it has been demonstrated in the case of aurora kinase that the gene duplication occurs in high frequency in cancer cells, and thus, this is expected to be an important cause of its activated expression. From these facts, fetal genes of this invention are thought to be involved in the malignant transformation of cells mediated by their activation due to the gene duplication or methylation of DNAs and so on.

Therefore, fetal genes and proteins encoded by the genes of this invention can be preferably used not only as the tool for purifying and cloning factors to control the cellular differentiation and proliferation but also as the target for screening candidate compounds of therapeutics and preventives for disorders such as tumors. In addition, the "fls353" and/or "fls485" genes can be applied to the medical treatment such as gene therapy in various cancers.

The term "substantially pure" as used herein in reference to a given polypeptide means that the polypeptide is substantially free from other biological macromolecules. For example, the substantially pure polypeptide is at least 75%, 80, 85, 95, or 99% pure by dry weight. Purity can be measured by any appropriate standard method known in the art, for example, by column chromatography, polyacrylamide gel electrophoresis, or HPLC analysis.

Accordingly, the invention includes a polypeptide having a sequence shown as SEQ ID NOs:2, 4 or 6. The invention also includes a polypeptide, or fragment thereof, that differs from the corresponding sequence shown as SEQ ID NOs:2, 4 or 6. The differences are, preferably, differences or changes at a non-essential residue or a conservative substitution. In one embodiment, the polypeptide includes an amino acid sequence at least about 60% identical to a sequence shown as SEQ ID NOs:2, 4 or 6, or a fragment thereof. Preferably, the polypeptide is at least 65%, 70%, 75%, 80%, 85%, 90%, 95%, 98%, 99% or more identical to SEQ ID NOs:2, 4 or 6 and has at least one cancer related or fetal function or activity described herein. Preferred polypeptide fragments of the invention are at least 10%, preferably at least 20%, 30%, 40%, 50%, 60%, 70%, or more, of the length of the sequence shown as SEQ ID NOs:2, 4 or 6 and have at least one cancer related or fetal activity described herein. Or alternatively, the fragment can be merely an immunogenic fragment.

This invention also includes proteins functionally equivalent to the human "fls353" or "fls485" proteins. Such proteins comprise, for example, homologous proteins from other organisms corresponding to the human "fls353" or "fls485" protein, and mutants of the human "fls353" or "fls485" protein.

In this invention, "functionally equivalent" means that a subject protein has functions related to cancer. Whether a protein has functions related to cancer or not can be characterized by, for example, its prominent expression specificity in cancer cell lines, fetal tissues or other tissues containing actively proliferating cells.

As a method well known by a person skilled in the art for preparing a protein functionally equivalent to a given protein, a method for introducing mutation into the protein is known. For example, one skilled in the art can prepare proteins functionally equivalent to the human "fls353" or "fls485" protein by introducing an appropriate mutation in the amino acid sequence of the human "fls353" or "fls485" protein by site-directed mutagenesis (Hashimoto-Gotoh et al., Gene,152:271–275, 1995; Zoller et al., Methods Enzymol., 100:468–500, 1983; Kramer et al., Nucleic Acids Res., 12:9441–9456, 1984; Kramer et al., Methods. Enzymol., 154:350–367, 1987; Kunkel, Proc. Natl. Acad. Sci. USA, 82:488–492, 1987; Kunkel, Methods Enzymol., 85:2763–2766, 1988). Mutation of amino acids could occur in nature, too. The protein of the present invention includes those comprising amino acid sequences of the human "fls353 or "fls485" protein in which one or more amino acids are mutated and functionally equivalent to the human "fls353" or "fls485" protein. It is considered that the number of amino acids to be mutated in such a mutant, is generally amino acids or less, preferably 5 amino acids or less, and more preferably 3 amino acids or less. Proteins having amino acid sequences modified by deleting, adding and/or replacing one or more amino acid residues of a certain amino acid sequence, have been known to retain the original biological activity (Mark et al., Proc. Natl. Acad. Sci. USA, 81:5662–5666, 1984; Zoller et al., Nucleic Acids Res., 10:6487–6500, 1982; Wang et al., Science, 224:1431–1433; Dalbadie-McFarland et al., Proc. Natl. Acad. Sci. USA, 79:6409–6413, 1982).

As for the amino acid residue to be mutated, it is preferable to be mutated into a different amino acid in which the properties of the amino acid side-chain are conserved. Examples of properties of amino acid side chains are, hydrophobic amino acids (A, I, L, M, F, P, W, Y, V), hydrophilic amino acids (R, D, N, C, E, Q, G, H, K, S, T), and amino acids comprising the following side chains: analiphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). (The parenthetic letters indicate the one-letter codes of amino acids.)

As a protein to which one or more amino acids residues are added to the amino acid sequence of human "fls353" or "fls485" protein (SEQ ID NOs:2, 4 or 6), for example, a fusion protein comprising human "fls353" or "fls485" protein can be used. Fusion proteins are fusions of the human "fls353" or "fls485" protein and other peptides or proteins, and are included in the present invention. Fusion proteins can be made by techniques well known to a person skilled in the art, such as by linking the DNA encoding the human "fls353" or "fls485" protein of the invention with DNA encoding other peptides or proteins, so as the frames match, inserting this into an expression vector and expressing it in a host. There is no restriction as to the peptides or proteins fused to the protein of the present invention.

Known peptides, for example, FLAG (Hopp et al., Biotechnology, 6:1204–1210, 1988), 6×His consisting of six His (histidine) residues, 10×His, Influenza agglutinin (HA), human c-myc fragment, VSV-GP fragment, p18HIV fragment, T7-tag, HSV-tag, E-tag, SV40T antigen fragment, lck tag, α-tubulin fragment, B-tag, Protein C fragment, and such, can be used as peptides that are fused to the protein of the present invention. Examples of proteins that are fused to protein of the present invention are, GST (glutalhione-S-transferase), Influenza agglutinin (HA), immunoglobulin constant region, β-galactosidase, MBP 20 (maltose-binding protein), and such.

Fusion proteins can be prepared by fusing commercially available DNA encoding these peptides or proteins with the DNA encoding the protein of the present invention and expressing the fused DNA prepared.

An alternative method known in the art to isolate functionally equivalent proteins is, for example, the method using a hybridization technique (Sambrook et al., Molecular Cloning 2nd ed., 9.47–9.58, Cold Spring Harbor Lab. Press, 1989). One skilled in the art can readily isolate DNA having high homology with a whole or part of the DNA sequence (SEQ ID NOs:1, 3 or 5) encoding the human "fls353" or "fls485" protein, and isolate functionally equivalent proteins to the human "fls353" or "fls485" protein from the isolated DNA. The proteins of the present invention include those encoded by DNA that hybridizes with a whole or part of the DNA sequence encoding human "fls353" or "fls485" protein and functionally equivalent to the human "fls353" or "fls485" protein. These proteins include a homologue of mammals corresponding to the protein derived from human (for example, a protein encoded by a monkey, rat, mouse, rabbit and bovine gene). When a cDNA highly homologous with the DNA encoding human "fls353" or "fls485" protein is isolated from animals, especially fetal tissues, fetal liver or kidney particularly preferable.

As used herein, an "isolated nucleic acid" is a nucleic acid, the structure of which is not identical to that of any naturally occurring nucleic acid or to that of any fragment of a naturally occurring genomic nucleic acid spanning more than three genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in random, uncharacterized mixtures of different DNA molecules, transfected cells, or cell clones, e.g., as these occur in a DNA library such as a cDNA or genomic DNA library.

Accordingly, in one aspect, the invention provides an isolated or purified nucleic acid molecule that encodes a polypeptide described herein or a fragment thereof. Preferably, the isolated nucleic acid molecule includes a nucleotide sequence that is at least 60% identical to the nucleotide sequence shown in SEQ ID NOs:1, 3 or 5. More preferably, the isolated nucleic acid molecule is at least 65%, 70%, 75%, 80%, 85%, 90%, 91%, 92%, 93%, 94%, 95%, 96%, 97%, 98%, 99%, or more, identical to the nucleotide sequence shown in SEQ ID NOs:1, 3 or 5. In the case of an isolated nucleic acid molecule which is longer than or equivalent in length to the reference sequence, e.g., SEQ ID NOs:1, 3 or 5, the comparison is made with the full length of the reference sequence. Where the isolated nucleic acid molecule is shorter that the reference sequence, e.g., shorter than SEQ ID NOs:1, 3 or 5, the comparison is made to a segment of the reference sequence of the same length (excluding any loop required by the homology calculation).

As a condition of hybridization for isolating a DNA encoding a protein functionally equivalent to human "fls353" or "fls485" protein, a person skilled in the art can conveniently select. One example of the hybridization condition for isolating functionally equivalent proteins is as follows. That is, after prehybridization at 55° C. for 30 minutes or more, hybridization is performed by adding labeled probes and incubating at 37 to 55° C. for an hour or more using "ExpressHyb Hybridization Solution" (CLONTECH). After that, the resulting hybridized product is washed three times for 20 minutes each at room temperature in 2×SSC and 0.1% SDS then once at 37° C. in 1×SSC and 0.1% SDS.

More preferably (more stringently), after prehybridization at 60° C. for 30 minutes or more, hybridization is performed by adding labeled probes and incubating at 60° C. for an hour or longer using "ExpressHyb Hybridization Solution" (CLONTECH). Thereafter, the hybridized product is washed three times for 20 minutes each at room temperature in 2×SSC and 0.1% SDS then twice at 50° C. in 1×SSC and 0.1% SDS.

Still more preferably (still more stringently), after prehybridization at 68° C. for 30 minutes or more, hybridization is performed by adding labeled probes and incubating at 68° C. for an hour or more using "ExpressHyb Hybridization Solution" (CLONTECH). Thereafter, the hybridized product is washed three times for 20 minutes each at room temperature in 2×SSC and 0.1% SDS then twice at 50° C. in 0.1×SSC and 0.1% SDS.

However, several factors such as temperature or salt concentration can influence the stringency of hybridization and one skilled in the art can suitably select the factors to accomplish a similar stringency. In place of hybridization, the gene amplification method using a primer synthesized based on the sequence information of the DNA (SEQ ID NOs:1, 3 or 5) encoding the human "fls353" or "fls485" protein, for example, the polymerase chain reaction (PCR) method can be utilized to isolate a DNA encoding the human "fls353" or "fls485" protein.

Proteins that have functionally equivalent as human "fls353" or "fls485" protein encoded by the DNA isolated through the above hybridization technique or gene amplification techniques, usually have a high homology to the amino acid sequence of the human "fls353" or "fls485" protein. "High homology" refers to, usually a homology of 60% or higher, preferably 70% or higher, more preferably 80% or higher, even more preferably 90% or higher. The homology of a protein can be determined by following the algorithm in "Wilbur et al., Proc. Natl. Acad. Sci. USA, 80:726–730, 1983".

As used herein, "% identity" of two amino acid sequences, or of two nucleic acid sequences, is determined using the algorithm of Karlin and Altschul (Proc. Natl. Acad. Sci. USA, 87:2264–2268, 1990), modified as in Karlin and Altschul, Proc. Natl. Acad. Sci. USA, 90:5873–5877, 1993). Such an algorithm is incorporated into the NBLAST and XBLAST programs of Altschul et al. (J. Mol. Biol., 215:403–410, 1990). BLAST nucleotide searches are performed with the NBLAST program, score=100, wordlength=12. BLAST protein searches are performed with the XBLAST program, score=50, wordlength=3. To obtain gapped alignment for comparison purposes Gapped-BLAST is utilized as described in Altschul et al. (Nucleic Acids Res., 25:3389–3402, 1997). When utilizing BLAST and GappedBLAST programs the default parameters of the respective programs (e.g., XBLAST and NBLAST) are used to obtain nucleotide sequences homologous to a nucleic acid molecule of the invention.

A protein of the present invention may have variations in amino acid sequence, molecular weight, isoelectric point, the presence or absence of sugar chains, or form, depending on the cell or host used to produce it or the purification method utilized. Nevertheless, as long as it has similar function as human "fls353" or "fls485" protein (SEQ ID NOs:2, 4 or 6) of the present invention, it is within the scope of the present invention.

The proteins of the present invention can be prepared as a recombinant protein or a natural protein by the method well known by the person skilled in the art. A recombinant DNA can be prepared by inserting a DNA (for example, the DNA comprising the nucleotide sequence of SEQ ID NOs:1, 3 or 5) which codes the protein of the present invention into an appropriate vector, collecting a recombinant obtained by introducing the vector into appropriate host cells, obtaining the extract, and purifying by subjecting the extract to chromatography such as ion exchange, reverse, gel filtration, or affinity chromatography in which an antibody against the protein of the present invention is fixed on column or by combining more than one of these columns.

Also when the protein of the present invention is expressed within host cells (for example, animal cells and *E. coli*) as a fusion protein with glutathione-S-transferase protein or as a recombinant protein supplemented with multiple histidines, the expressed recombinant protein can be purified using a glutathione column or nickel column.

After purifying the fusion protein, it is also possible to exclude regions other than the objective protein by cutting with thrombin or factor-Xa as required. A natural protein can be isolated by the method known by a person skilled in the art, for example, by effecting the affinity column in which the antibody binding to the human "fls353" or "fls485" protein described below is bound against the extract of tissues or cells expressing the protein of the present invention is expressed. An antibody can be a polyclonal or a monoclonal antibody.

The present invention also contains a partial peptide of the protein of the present invention. A partial peptide comprising the amino acid sequence specific to the protein of the present invention comprises at least 7 amino acids, preferably 8 amino acids or more, and more preferably 9 amino acids or more. The partial peptide can be used, for example, for preparing an antibody against the protein of the present invention, screening a compound biding to the protein of the present invention, and for screening accelerators or inhibitors of the protein of the present invention.

A partial peptide of the invention can be produced by genetic engineering, known methods of peptide synthesis, or by digesting the protein of the invention with an appropriate peptidase. For peptide synthesis, for example, solid phase synthesis or liquid phase synthesis may be used.

Furthermore, the present invention relates to a DNA encoding the protein of the present invention as described. The DNA of the present invention can be used for the production of the protein of the present invention in vivo or in vitro as described above as well as for, for example, application to the gene therapy for diseases attributed to genetic abnormality in the gene encoding the protein of the present invention. Any form of the DNA of the present invention can be used as long as it encodes the protein of the present invention. Specifically, DNA synthesized from the mRNA, genomic DNA, or chemically synthesized DNA can be used. The present invention includes a DNA comprising a given nucleotide sequence based on degeneracy of genetic codons, as long as it encodes the protein of the present invention.

The DNA of the present invention can be prepared by the method known by a person skilled in the art. For example, the DNA of the present invention can be prepared by preparing a cDNA library from cells which express the protein of the present invention, and conducting hybridization by using a partial sequence of the DNA of the present invention (e.g., SEQ ID NOs:1, 3, or 5) as a probe. A cDNA library can be prepared, for example, by the method described in Sambrook et al., Molecular Cloning, Cold Spring Harbor Laboratory Press (1989), or by using a cDNA library in the market. A cDNA library can be also prepared by preparing RNA from cells expressing the protein of the present invention, synthesizing an oligo DNA base on the sequence of the DNA of the present invention (for example, SEQ ID NOs:1, 3 or 5), conducting PCR by using these as primers, and amplifying cDNA encoding the protein of the present invention.

In addition, by sequencing the nucleotides of the obtained cDNA, a translation region encoded by this can be determined, and an amino acid sequence of the protein of the present invention can be obtained. Moreover, by screening the genomic DNA library using the obtained cDNA as a probe, genomic DNA can be isolated.

More specifically, mRNAs may first be prepared from a cell, tissue, or organ (for example, fetal liver or kidney, carcinoma clone and so on) in which the protein of the invention is expressed. Known methods can be used to isolate mRNAs, for instance, total RNA is prepared by guanidine ultracentrifugation (Chirgwin et al., Biochemistry, 18:5294–5299, 1979) or AGPC method (Chomczynski et al., Anal. Biochem., 162:156–159, 1987), and mRNA is purified from total RNA using mRNA Purification Kit (Pharmacia) and such. Alternatively, mRNA may be directly purified by QuickPrep mRNA Purification Kit (Pharmacia).

The obtained mRNA is used to synthesize cDNA using reverse transcriptase. cDNA may be synthesized by using a kit such as the AMV Reverse Transcriptase First-strand cDNA Synthesis Kit (Seikagaku Kogyo). Alternatively, cDNA may be synthesized and amplified following the 5'-RACE method (Frohman et al., Proc. Natl. Acad. Sci. USA, 85:8998–9002, 1988); Belyavsky et al., Nucleic Acids Res., 17:2919–2932, 1989) which uses a primer and such, described herein, the 5'-Ampli FINDER RACE Kit (CLONTECH), and polymerase chain reaction (PCR).

A desired DNA fragment is prepared from the PCR products and ligated with a vector DNA. The recombinant vectors are used to transform *E. coli* and such, and a desired recombinant vector is prepared from a selected colony. The nucleotide sequence of the desired DNA is able to verify by conventional methods, such as dideoxynucleotide chain termination.

A DNA of the invention may be designed to have a sequence that is expressed more efficiently by taking into account the frequency of codon usage in the host to be used for expression (Grantham et al., Nucleic Acids Res., 9:43–74, 1981). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG).

Specifically, DNAs of this invention include DNAs comprising the bases A472 through C2712 in the nucleotide sequence set forth in SEQ ID NO:1, the bases A247 through G1305 in the nucleotide sequence set forth in SEQ ID NO:3, and the bases A254 through G1159 in the nucleotide sequence set forth in SEQ ID NO:5.

Furthermore, the present invention provides DNA that is capable of hybridizing with DNA having a nucleotide sequence of SEQ ID NOs:1, 3 or 5 under stringent conditions, and encoding a protein functionally equivalent to the protein of the invention described above.

Stringent conditions may be appropriately chosen by one skilled in the art, and, for example, low stringent conditions can be used. More preferably, high stringent conditions can be used. These conditions are the same as the above. The above hybridizing DNA is preferably a cDNA or chromosomal DNA.

The present invention also relates to a vector into which the DNA of the present invention is inserted. The vector of the present invention is useful to keep DNA of the present invention in host cell, or to express the protein of the present invention.

When *E. coli* is a host cell and the vector is amplified and produced in a large amount in *E. coli* (e.g., JM109, DH5α, HB101, or XL1Blue), the vector should have "ori" to be amplified in *E. coli* and a marker gene for selecting transformed *E. coli* (e.g., a drug-resistance gene selected by a drug (e.g., ampicillin, tetracycline, kanamycin, or chloramphenicol)). For example, M13-Series vectors, pUC-series vectors, pBR322, pBluescript, pCR-Script, and so on can be used. For example, pGEM-T, pDIRECT, and pT7 can also be used for subcloning and extracting cDNA as well as the vectors described above. When a vector is used to produce the protein of the present invention, an expression vector is especially useful. For example, an expression vector to be expressed in *E. coli* should have the above characteristics to be amplified in *E. coli*. When *E. coli*, such as JM109, DH5α, HB101, or XL1 Blue, are used as a host cell, the vector should have a promoter as well as the above characters such as the vector is copied in the host, for example, lacZ promotor (Ward et al., Nature, 341:544–546, 1989; FASEB J., 6:2422–2427, 1992), araB promoter (Better et al., Science, 240:1041–1043, 1988), or T7 promoter and such, that can efficiently express the desired gene in *E. coli*. As such a vector, for example, pGFX-5X-1 (Pharmacia), "QIAexpress system" (Qiagen), pEGFP or pET (in this case, a host is preferably BL21 which expresses T7 RNA polymerase) can be used besides the above vectors.

A vector also may contain a signal sequence for polypeptide secretion. As a signal sequence for protein secretion, pelB signal sequence (Lei et al., J. Bacterial., 169:4379, 1987) can be used in the case of producing periplasm in *E. coli*. For introducing a vector into host cells, for example, calcium chloride method, and electroporation method can be used.

Besides *E. coli*, for example, expression vectors derived from mammals (for example, pcDNA3 (Invitrogen) and pEGF-BOS (Nucleic Acids Res., 18:5322, 1990), pEF, pCDM8), expression vectors derived from insect cells (for example, "Bac-to-Bac baculovirus expression system" (GIBCO BRL), pBacPAK8), expression vectors derived from plants (for example, pMH1, pMH2), expression vectors derived from animal viruses (for example, pHSV, pMV, pAdexLcw), expression vectors derived from retroviruses (for example, pZIPneo), expression vector derived from yeast (for example, "Pichia Expression Kit" (Invitrogen), pNV11, SP-Q01), expression vectors derived from *Bacillus subtilis* (for example, pPL608, pKTH50) can be used for producing the protein of the present invention.

In order to express the vector in animal cells, such as CHO, COS, or NIH3T3 cells, the vector should have a promoter necessary for expression in such cells, for example, SV40 promoter (Mulligan et al., Nature, 277:108, 1979), MMLV-LTR promoter, EF1α promoter (Mizushima et al., Nucleic Acids Res., 18:5322, 1990), or CMV promoter, and such, and preferably a marker gene for selecting transformants (for example, a drug resistance gene selected by a drug (e.g., neomycin, G418)). Examples of the vectors with these characteristics include pMAM, pDR2, pBK-RSV, pBK-CMV, pOPRSV, and pOp13 and so on.

In addition, for the purpose of expressing a gene stably and amplifying the copy number of the gene in cells, for example, the method for introducing a vector comprising the complementary DHFR gene (for example, pCH0 I), into CHO cells in which nuclei acid synthesizing pathway is deleted and amplifying by methotrexate (MTX) can be used and in the case of transient expression of a gene, the method for transforming with a vector (e.g., pcD) comprising replication origin of SV40 using COS cells comprising the SV40 T antigen expressing gene on chromosomes can be used.

On the other hand, the DNA of the present invention can be expressed in vivo in animals, for example, by inserting the DNA of the present invention into an appropriate vector and introducing in vivo by such as retrovirus method, liposome method, cationic liposome method, adenovirus method. By using these, gene therapy against diseases attributed to mutation of "fls353" or "fls485" gene of the present invention can be effected. As a vector to be used, for example, adenovirus vector (for example, pAdexlcw), and retrovirus vector (for example, pZIPneo) can be used, but not restricted thereto. Common gene manipulation, for example, insertion of the DNA of the present invention to a vector, can be performed according to the standard method (Sambrook, J. et al. Molecular Cloning 2nd ed., 5. 61–5. 63, Cold Spring Harbor Lab. Press, 1989). Administration into a living body can be either ex vivo method, or in vivo method.

The present invention relates to a host cell into which the vector of the present invention has been introduced. The host cell into which the vector of the invention is introduced is not particularly limited. *E. coli* or various animal cells can be used. The host cells of the present invention can be used for, for example, production system for producing or expressing the protein of the present invention. The present invention provides methods of producing a protein of the invention both in vitro or in vivo. For in vitro production, eukaryotic cells or prokaryotic cells can be used as host cells.

Useful eukaryotic cells as host may be animal, plant, or fungi cells. As animal cells, mammalian cells such as CHO (J. Exp. Med., 108:945,1995), COS, 3T3, myeloma, baby hamster kidney (BHK), HeLa, Vero cells, or amphibian cells such as Xenopus oocytes (Valle, et al., Nature, 291:340–358, 1981), or insect cells such as sf9, sf21, or Tn5 cells can be used. CHO cells lacking DHFR gene (dhfr-CHO) (Proc. Natl. Acad. Sci. USA, 77:4216–4220, 1980) or CHO K-1 (Proc. Natl. Acad. Sci. USA, 60:1275, 1968) may also be used. In animal cells, CHO cells are particularly preferable for the mass expression. A vector can be introduced into host cells by, for example, calcium phosphate method, DEAE dextran method, cationic liposome DOTAP (Boehringer Mannheim), electroporation method, lipofection method. As plant cells, plant cells originating from *Nicotiana tabacum* are known as protein-production system, and may be used as callus cultures. As fungi cells, yeast cells such as *Saccharomyces*, including *Saccharomyces cerevisiae*, or filamentous fungi such as *Aspergillus*, including *Aspergillus niger*, are known and may be used herein.

Useful prokaryotic cells include bacterial cells, such as *E. coli*, for example, JM109, DH5α, HB101 are known. Others, *Bacillus subtilis* is known.

These cells are transformed by a desired DNA, and the resulting transformants are cultured in vitro to obtain the protein. Transformants can be cultured using known methods. Culture medium for animal cell, for example, DMEM, MEM, RPMI1640, or IMDM may be used with or without serum supplement such as fetal calf serum (FCS). The pH of the culture medium is preferably between about pH 6 to 8. Such cells are typically cultured at about 30 to 40° C. for about 15 to 200 hr, and the culture medium may be replaced, aerated, or stirred if necessary.

Animal and plant hosts may be used for in vivo production. For example, a desired DNA can be introduced into an animal or plant host. Encoded proteins are produced in vivo, and then recovered. These animal and plant hosts are included in host cells of the present invention.

Animals to be used for the production system described above include, but are not limited to, mammals and insects. Mammals such as goat, porcine, sheep, mouse, and bovine may be used (Vicki Glaser, SPECTRUM Biotechnology Applications (1993)). Alternatively, the mammals may be transgenic animals.

For instance, a desired DNA may be prepared as a fusion gene with a gene encoding a protein specifically produced into milk, such as goat β casein. DNA fragments comprising the fusion gene having the desired DNA are injected into goat embryos, which are then introduced back to female goats. Proteins are recovered from milk produced by the transgenic goats (i.e., those born from the goats that had received the modified embryos) or from their offspring. To increase the amount of milk containing the proteins produced by transgenic goats, appropriate hormones may be administered to them (Ebert et al., Bio/Technology, 12:699–702, 1994).

Alternately, insects, such as the silkworm, may be used. A desired DNA inserted into baculovirus can be used to infect silkworms, and the desired protein is recovered from their body fluid (Susumu et al., Nature, 315:592–594, 1985).

As plants, for example, tobacco can be used. In use of tobacco, a desired DNA may be inserted into a plant expression vector, such as pMON530, which is introduced into a bacteria, such as *Agrobacterium tumefaciens*. Then the bacteria is used to infect tobacco, such as *Nicotiana tabacum*, and a desired polypeptide is recovered from their leaves (Julian et al., Eur. J. Immunol., 24:131–138, 1994).

A protein of the present invention obtained as above may be isolated from inside or outside (e.g., medium) of cells or hosts, and purified as substantially pure homogeneous protein. The method for protein isolation and purification is not limited to any specific method; in fact, any standard method may be used. For instance, column chromatography, filter, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

For chromatography, for example, affinity chromatography, ion-exchange chromatography, hydrophobic chromatography, gel filtration, reverse phase chromatography, adsorption chromatography, and such may be used (Strategies for Protein Purification and Characterization: A Laboratory Course Manual. Ed, Daniel R. Marshak et al., Cold Spring Harbor Laboratory Press (1996)). These chromatographies may be performed by liquid chromatography such as HPLC and FPLC. Thus, the present invention provides for highly purified proteins, produced by the above methods.

A protein of the present invention may be optionally modified or partially deleted by treating it with an appropriate protein modification enzyme before or after purification. Useful protein modification enzymes include, but are not limited to, trypsin, chymotrypsin, lysylendopeptidase, protein kinase, and glucosidase.

The present invention relates to an antibody that binds to the protein of the invention. The antibody of the invention can be used in any form, such as monoclonal or polyclonal antibodies, and includes antiserum obtained by immunizing a rabbit with the protein of the invention, all classes of polyclonal and monoclonal antibodies, human antibodies, and humanized antibodies produced by genetic recombination.

A protein of the invention used as an antigen to obtain an antibody may be derived from any animal species, but preferably from a mammal such as a human, mouse, or rat, or more preferably from a human. A human-derived protein may be obtained from the nucleotide or amino acid sequences disclosed herein.

In the present invention, a protein to be used as an immunization antigen may be a complete protein or a partial peptide of the protein. A partial peptide may be, for example, an amino (N)-terminal or carboxy (C)-terminal fragment of the protein. Herein, "an antibody" is defined as an antibody that specifically reacts with either the full length or a fragment of the protein.

A gene encoding a protein of the invention or its fragment may be inserted into a known expression vector, which is used to transform a host cell as described herein. The desired protein or its fragment may be recovered from the outside or inside of host cells by any standard method, and may be used as an antigen. Alternatively, cells expressing the protein or their lysates, or a chemically synthesized protein may be used as an antigen.

Any mammalian animal may be immunized with the antigen, but preferably the compatibility with parental cells used for cell fusion is taken into account. In general, animals of Rodentia, Lagomorphs, or Primates are used.

Animals of Rodentia include, for example, mouse, rat, and hamster. Animals of Lagomorphs include, for example, rabbit. Animals of Primates include, for example, a monkey of catarrhine (old world monkey) such as *Macaca fascicularis*, rhesus monkey, sacred baboon, or chimpanzee.

Methods for immunizing animals against antigens are known in the art. Intraperitoneal injection or subcutaneous injection of antigens is used as a standard method for immunization of mammals. More specifically, antigens may be diluted and suspended in an appropriate amount with phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of antigen mixed with an appropriately amount of Freund's incomplete adjuvant every 4 to 21 days. An appropriate carrier may also be used for immunization. After immunization as above, serum is examined for increase of the amount of desired antibodies by a standard method.

Polyclonal antibodies against the proteins of the present invention may be prepared by collecting blood from the immunized mammal examined for the increase of desired antibodies in the serum, and by separating serum from the blood by any conventional method. Polyclonal antibodies may be used as serum containing the polyclonal antibodies, or if necessary, a fraction containing the polyclonal antibodies may be isolated from the serum. Immunoglobulin G or M can be prepared by obtaining a fraction which recognizes only the protein of the present invention using an affinity column coupled with the protein of the present invention and further purifying this fraction by using protein A or protein G column.

To prepare monoclonal antibodies, immune cells are collected from the mammal immunized against the antigen and checked for the increased level of desired antibodies in the serum as described above, and are subjected to cell fusion. The immune cells used for cell fusion are preferably obtained from spleen. As the other parental cells to be fused with the above immunocyte, for example, preferably myeloma cells of mammalians, and more preferably myeloma cells which acquired the property for selecting fused cells by drugs can be used.

The above immunocyte and myeloma cells can be fused by the known method, for example, the method by Milstein et al. (Methods Enzymol., 73:3–46, 1981).

Resulting hybridomas obtained by the cell fusion may be selected by cultivating them in a standard selection medium, such as HAT medium (medium containing hypoxanthine, aminopterin, and thymidine). The cell culture is typically continued in the HAT medium for several days to several weeks, the sufficient time to allow all the other cells, except desired hybridoma (non-fused cells), to die. Then, by the standard limiting dilution method, a hybridoma cell producing the desired antibody is screened and cloned.

Besides the above method, in which a non human animal is immunized against an antigen for preparing hybridoma, human lymphocytes such as that infected by EB virus may be immunized with a protein, protein expressing cells, or their lysates in vitro. Then, the immunized lymphocytes are fused with human-derived myeloma cells capable of indefinitely dividing, such as U266, to yield a hybridoma producing a desired human antibody having binding ability to the protein can be obtained (Unexamined Published Japanese Patent Application (JP-A) No. Sho 63-17688).

Next, the monoclonal antibody obtained by transplanting the obtained hybridomas into the abdominal cavity of a mouse and by extracting ascites can be purified by, for example, ammonium sulfate precipitation, protein A or protein G column, DEAE ion exchange chromatography, or an affinity column to which the protein of the present invention is coupled. The antibody of the present invention can be used not only for purification and detection of the protein of the present invention, but also as a candidate for agonists and antagonists of the protein of the present invention. In addition, this antibody can be applied to the antibody treatment for diseases involved by the protein of the present invention. When the obtained antibody is used for the administration to the human body (antibody treatment), a human antibody or a humanized antibody is preferable for reducing immunogenicity.

For example, transgenic animals having a repertory of human antibody genes may be immunized against a protein, protein expressing cells, or their lysates as an antigen. Antibody producing cells are collected from the animals, and fused with myeloma cells to obtain hybridoma, from which human antibodies against the protein can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, for example, Borrebaeck C. A. K. and Larrick, J. W., THERAPEUTIC MONOCLONAL ANTIBODIES, published in the United Kingdom by MACMILLAN PUBLISHERS LTD (1990)). A DNA encoding an antibody may be cloned from an immune cell such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, so long as it binds to one or more of the proteins of the invention. For instance, the antibody fragment may be Fab, F (ab')$_2$, Fv, or single chain Fv (scFv), in which Fv fragments from H and L chains are ligated by an appropriate linker (Huston et al,. Proc. Natl. Acad. Sci. USA, 85:5879–5883, 1988). More specifically, an antibody fragment may be generated by treating an antibody with an enzyme such as papain or pepsin. Alternatively, a gene encoding the antibody fragment may be constructed, inserted into an expression vector, and expressed in an appropriate host cell (see, for example, Co et al., J. Immunol., 152:2968–2976, 1994; Retter et al., Methods Enzymol., 178:476–496, 1989; Pluckthun et al., Methods Enzymol., 178:497–515, 1989; Lamoyi, E., Methods Enzymol., 121:652–663, 1986; Rousseaux et al., Methods Enzymol., 121:663–669, 1986; Bird et al., Trends Biotechnol., 9:132–137, 1991).

An antibody may be modified by conjugation with a variety of molecules, such as polyethylene glycol (PEG). The present invention provides such modified antibodies. The modified antibody can be obtained by chemically modifying an antibody. These modification methods are conventional in this field.

Alternatively, an antibody of the present invention may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region.

Obtained antibodies may be purified into homogeneity. The antibody used in the present invention can be separated and purified by used for separating and purifying usual proteins. For example, the separation and purification of the protein can be performed by the appropriately selected and combined use of column chromatography such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but the methods are not limited thereto.

Examples of columns used for affinity chromatography include protein A column and protein G column. Examples of columns using protein A column include Hyper D, POROS, Sepharose F. F, (Pharmacia), etc.

Besides affinity chromatography, the chromatography includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al, Cold Spring Harbor Laboratory Press. 1996). The chromatographic procedures can be carried out by liquid-phase chromatography such as HPLC, FPLC, or the like.

For example, measurement of absorbance, enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody, that recognizes the primary antibody is labeled with an enzyme such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment, may be used as a protein. BIAcore (Pharmacia) may be used to evaluate the activity of the antibody according to the present invention.

The above methods allow for the detection or measurement of the protein of the invention, by exposing the antibody of the invention to a sample assumed to contain the protein of the invention, and detecting or measuring the immune complex formed by the antibody and the protein.

Because the method of detection or measurement of proteins according to the invention can specifically detect or measure proteins, the method may be useful in a variety of experiments in which the protein is used.

The present invention relates a nucleotide which hybridizes with the DNA encoding human "fls353" or "fls485" protein (SEQ ID NOs:1, 3 or 5) or the complementary strand, and comprises at least 15 nucleotides. The nucleotide of the present invention is preferably the nucleotide which specifically hybridizes with the DNA encoding the protein of the present invention. The term "specifically hybridize" as used herein, means that cross-hybridization does not occur significantly with DNA encoding other proteins, in the above-mentioned hybridizing conditions, preferably under stringent hybridizing conditions. Such nucleotide includes, probes, primers, nucleotides and nucleotide derivatives (for example, antisense oligonucleotides and ribozymes and so on), which specifically hybridize with DNA encoding the protein of the invention or its complementary strand. Moreover, such nucleotide can utilize as preparation of DNA chip.

The present invention includes an antisense oligonucleotide that hybridizes with any site within the nucleotide sequence any one of SEQ ID NOs:1, 3 and 5. This antisense oligonucleotide is preferably that against the at least 15 continuous nucleotides in the nucleotide sequence anyone of SEQ ID NOs:1, 3 or 5. The above-mentioned antisense oligonucleotide, which contains an initiation codon in the above-mentioned at least 15 continuous nucleotides, is even more preferred.

Derivatives or modified products of antisense oligonucleotides can be used as antisense oligonucleotides. Examples of such modified products are, lower alkyl phosphonate modifications such as methyl-phosphonate-type or ethyl-phosphonate-type, phosphothioate modifications and phosphoamidate modifications.

The term "antisense oligonucleotides" as used herein means, not only those in which the entire nucleotides corresponding to those constituting a specified region of a DNA or mRNA are complementary, but also those having a mismatch of one or more nucleotides, as long as DNA or mRNA and an oligonucleotide can specifically hybridize with the nucleotide sequence of SEQ ID NOs:1, 3 or 5.

Such nucleotides have a homology of at least 70%, preferably at least 80%, more preferably 90% or higher, even more preferably 95% or higher in the at least 15 continuous nucleotide sequence region. The algorithm stated herein can be used to determine homology. Such oligonucleotides are useful as probes for the isolation or detection of DNA encoding the protein of the invention as stated in a later example or as a primer used for amplifications.

The antisense oligonucleotide derivative of the present invention has inhibitory effect on the function of the protein of the present invention as a result that the derivative inhibits the expression of the protein of the invention by acting upon cells producing the protein of the invention and by binding to the DNA or mRNA encoding the protein to inhibit its transcription or translation or to promote the degradation of the mRNA.

The antisense oligonucleotide derivative of the present invention can be made into an external preparation such as a liniment and a poultice by mixing with a suitable base material which is inactive against the derivatives.

Also, as necessary, the derivatives can be formulated into tablets, powders, granules, capsules, liposome capsules, injections, solutions, nose-drops, and freeze-drying agents and such by adding excipients, isotonic agents, solubilizing agents, stabilizers, preservative substance, pain-killers, and such. These can be prepared by following usual methods.

The antisense oligonucleotide derivative is given to the patient by directly applying onto the ailing site or by injecting into a blood vessel so that it will reach the site of ailment. An antisense-mounting medium can also be used to increase durability and membrane-permeability. Examples are, liposome, poly-L-lysine, lipid, cholesterol, lipofectin or derivatives of these.

The dosage of the antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

The antisense oligonucleotide of the invention inhibits the expression of the protein of the invention and thereby useful for suppressing the biological activity of the protein of the invention. Also, expression-inhibitors comprising the antisense oligonucleotide of the invention are useful in that they can inhibit the biological activity of the protein of the invention. It is thought it possible to use antisense oligonucleotides of this invention for the purpose of antineoplastic.

Moreover the present invention relates to a method for screening a compound binding to the protein of the present invention by using the protein of the present invention. This screening method contains the steps of: (a) contacting a test sample with the protein of the present invention or a partial peptide thereof, (b) detecting a binding activity of the test sample to the protein of the present invention or the partial peptide thereof, and (c) selecting a compound which binds to the protein of the present invention or the partial peptide thereof.

The protein of the present invention to be used for screening may be a recombinant protein, a protein derived from the nature, or the partial peptide thereof. Any test sample, for example, cell extracts, cell culture supernatant, products of fermenting microorganism, extracts from marine organism, plant extracts, purified or crude proteins, peptides, non-peptide compounds, synthetic low molecular compounds and natural compounds, can be used. The protein of the present invention to be contacted with a test sample can be contacted, for example, as a purified protein, a soluble protein, a form bound to a carrier, or a fusion protein with another protein.

By using the protein of the present invention, for example, as a method for screening a protein binding to the protein thereof, many methods well known by a person skilled in the art can be used. Such a screening can be conducted by, for example, immunoprecipitation method, specifically, in the following manner. The gene encoding the protein of the present invention is expressed in such as animal cells by inserting the gene to a expression vector for foreign gene, such as pSV2neo, pcDNA I, pCD8. As a promoter to be used for the expression, any promoter which can be used in general can be selected, for example, SV40 early promoter (Rigby in Williamson (ed.), Genetic engineering, vol. 3. Academic Press, London, p. 83–141 (1982)), EF-1α promoter (Kim et al., Gene, 91:217–223, 1990), CAG promoter (Niwa et al., Gene, 108:193–200, 1991), RSV LTR promoter (Cullen, Methods in Enzymology, 152:684–704, 1987), SRα promoter (Takebe et al, Mol. Cell. Boil., 8:466, 1988), CMV immediate early promoter (Seed et al., Proc. Natl. Acad. Sci. USA, 84:3365–3369, 1987), SV40 late promoter (Gheysen et al., J. Mol. Appl. Genet., 1:385–394, 1982), Adenovirus late promoter (Kaufman et al., Mol. Cell. Biol., 9:946, 1989), HSV TK promoter and so on. To express a foreign gene by introducing the gene into animal cells, electroporation method (Chu et al., Nucl. Acid Res., 15:1311–1326, 1987), calcium phosphate method (Chen et al., Mol. Cell. Biol., 7:2745–2752, 1987), DEAE dextran method (Lopata et al., Nucl. Acids Res., 12:5707–5717, 1984; Sussman, et al., Mol. Cell. Biol., 4:1642–1643, 1985), Lipofectin method (Derijard, Cell, 7:1025–1037, 1994; Lamb et al., Nature Genetics, 5:22–30, 1993; Rabindran et al., Science, 259:230–234, 1993), and such can be exemplified, and any method can be used. The protein of the present invention can be expressed as a fusion protein comprising an a recognition site (epitope) of monoclonal antibody by introducing the epitope of the monoclonal antibody which property has been revealed to N or C terminus of the protein of the present invention. An epitope-antibody system in the market can be used (Experimental Medicine, 13:85–90, 1995). Through a multiple cloning site, a vector which can express a fusion protein with, for example, β-galactosidase, maltose binding protein, glutathione S-transferase, green florescence protein (GFP), is available in the market.

Methods have been reported in which a fusion protein is prepared by introducing only small epitopes comprising several to ten and several amino acids so that properties of the protein of the present invention may not change by making the protein a fusion protein. Epitopes, for example, polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), epitope such as E-tag (an epitope on monoclonal phage), and monoclonal antibodies recognizing these can be, used as an epitope-antibody system for screening a protein binding to the protein of the present invention (Experimental Medicine, 13:85–90, 1995).

In the immunoprecipitation, an immune complex is formed by adding these antibodies to cell eluate prepared by using an appropriate detergent. This immune complex comprises the protein of the present invention, a protein comprising the binding ability with the protein, and an antibody. Immunoprecipitation can be conducted by an antibody against the protein of the present invention, besides using antibodies against the above epitopes. An antibody against the protein of the present invention can be prepared, for example by introducing a gene encoding the protein of the present invention to an appropriate E. coli expression vector, expressing the gene in E. coli, purifying the expressed protein, and immunizing the protein to for example, rabbits, mice, rats, goats, and domestic fowls and such. The antibody can be prepared also by immunizing the above animals against a synthesized partial peptide of the protein of the present invention.

An immune complex can be precipitated, for example by Protein A Sepharose or Protein G Sepharose when an antibody is mouse IgG antibody. When the protein of the present invention is prepared as a fusion protein with an epitope, for example GST, an immune complex can be formed by using a substance specifically binding to these epitopes, such as glutathione-Sepharose 4B in the same manner as in the use of an antibody of the protein of the present invention.

Popular Immunoprecipitation can be performed by following or according to, for example, the reference (Harlow et al., Antibodies, 511–552, Cold Spring Harbor Laboratory publications, New York (1988)).

SDS-PAGE is commonly used for analysis of immunoprecipitated proteins and the binding protein can be analyzed depending on a molecular weight of the protein by using gel with an appropriate concentration. In general, because it is difficult to detect a protein binding to the protein of the present invention by a common staining method, such as Coomassie staining or silver staining, the detection sensitivity for the protein can be improved by culturing in the culture medium containing radioactive isomer, $^{35}$S-methionine or $^{35}$S-cystein, labeling proteins in the cells, and detecting the proteins. The target protein can be purified from SDS-polyacrylamide gel and its sequence can be determined directly after a molecular weight of the protein is determined.

As a method for isolating a protein binding to the protein of the present invention by using the protein, for example, West-Western blotting analysis (Skolnik et al., Cell, 65:83–90, 1991) can be used. That is, a protein binding to the protein of the present invention can be obtained by preparing a cDNA library from cells, tissues, organs (for example, fetal liver, fetal kidney or cancer cell strain, and so on) expected to express a binding protein bound to the protein of the present invention by using a phage vector (λgt11, ZAP), expressing the protein on LB-agarose, and fixing the protein expressed on the filter, reacting the purified and labeled protein of the present invention with the above vector, and detecting a plaques expressing proteins bound to the protein of the present invention by the label. As a method to label the protein of the invention is a method utilizing the binding between biotin and avidin, or a method utilizing an antibody that specifically binds to the protein of the present invention, or a peptide or polypeptide (for example, GST) that is fused to the protein of the present invention, and a method using radioisotope or fluorescence and such.

Alternatively, as another embodiment of the method of screening of the present invention is a two-hybrid system utilizing cells (Fields et al., Trends Genet., 10:286–292, 1994).

Proteins binding to the proteins of this invention or genes thereof can be prepared utilizing the "two-hybrid system" ("MATCHMAKER Two-Hybrid System", "Mammalian MATCHMAKER Two-Hybrid Assay Kit", "MATCHMAKER One-Hybrid System" (all from Clontech), "HybriZAP Two-Hybrid Vector System (Stratagene), (Dalton, S., and Treisman, R. (1992) Characterization of SAP-1, a protein recruited by serum response factor to the c-fos serum response element. Cell, 68:597–612), wherein the protein of this invention is made to be expressed in yeast cells as a protein fused to the DNA-binding domain of SRF or GAL4; a cDNA library is prepared from cells which are assumed to express proteins binding to the protein of this invention so as to express the protein of this invention in the form fused to the VP16 or GAL4 transcriptional activation domain; the library is transferred to the aforementioned yeast cells to isolate the library-derived cDNA from the positive clones detected, which is then transferred to and expressed in *E. coli* (when a protein binding to the protein of this invention is expressed in yeast cells, the reporter gene is activated due to the binding of both proteins, enabling the identification of positive clones.)

As a reporter gene, for example, Ade2 gene, lacZ gene, CAT gene, luciferase gene, can be used besides HIS3 gene.

A protein binding to the protein of the present invention can be screened by using an affinity chromatography. For example, the method for screening of the present invention utilizes affinity chromatography. The protein of the invention is immobilized on a carrier of an affinity column, and a test sample, in which a protein capable of binding to the protein of the invention is supposed to be expressed, is applied to the column. A test sample herein may be, for example, cell extracts, cell lysates, etc. After loading the test sample, the column is washed, and proteins bound to the protein of the invention can be prepared.

An amino acid sequence of the obtained protein is analyzed, an oligo DNA was synthesized based on the sequence, and cDNA libraries are screened using the DNA as a probe to obtain a DNA encoding the protein.

A biosensor using the Surface Plasmon Resonance phenomenon may be used as a mean for detecting or quantifying the bound compound in the present invention. When such a biosensor is used, the interaction between the protein of the invention and a test compound can be observed in real-time as a surface plasmon resonance signal, using only a minute amount of proteins without labeling (for example, BIAcore, Pharmacia). Therefore, it is possible to evaluate the binding between the protein of the invention and a test compound using a biosensor such as BIAcore.

The method of screening molecules that bind when the immobilized protein of the present invention is exposed to synthetic chemical compounds, natural substance banks, or a random phage peptide display library, or the method of screening using high-throughput based on combinatorial chemistry techniques (Wrighton et al., "Small peptides as potent mimetics of the protein hormone erythropoietin", Science, 273:458–64, 1996; Verdine, "The combinatorial chemistry of nature", Nature, 384:11–13, 1996; Hogan, "Directed combinatorial chemistry", Nature, 384:17–19, 1996) is well known to one skilled in the art as a method for isolating not only proteins but also chemical compounds that bind to protein of the present invention (including agonist and antagonist).

A compound isolated by the screening becomes a candidate for drugs which promote or inhibit the activity of the protein of the present invention, for treating or preventing of diseases attributed to, for example, functional abnormality of the protein of the present invention, or neoplasm. A substance obtained by converting, using addition, deletion and/or replacement, a part of the structure of a compound being obtained using the screening method of the present invention and having the activity to bind to the protein of the present invention is also included in compounds obtained using the screening method of the present invention.

In addition, using the genes encoding the proteins of this invention or the expression-controlling domains thereof, it is thought it possible to screen compounds which can suppress or promote the expression (including the transcription and translation) of these genes in vivo. This screening method can be utilized, for example, to screen candidate compounds for therapeutic and preventive products for cancer.

This screening can be performed by a method comprising the steps of: (a) contacting a test sample with cells expressing the genes of this invention, (b) detecting the expression of the genes of this invention in the cells, and (c) selecting a compound that decreases or increases the expression of the genes of this invention compared with that in the case where the test sample is not contacted with the cells (control).

Desired compounds can be screened, for example, by culturing a suitable cell strain which expresses the "fls353" or "fls485" gene (such as HeLa S3, Hep G2, etc.) together with a test sample and investigating the expression of these genes (including transcription and translation thereof) by detecting mRNA using northern blot technique or RT-PCR method, by detecting protein using western blotting, or these methods modified, and selecting compounds to increase or decrease the expression of these genes compared with the case where no test sample is added.

It is also possible to screen compounds to suppress or promote the gene expression of this invention in vivo by a method employing the activation or inactivation of the expression-controlling domain for the gene of this invention as an indicator. This screening can be implemented by a method comprising the steps of (a) providing cells into which a vector comprising a reporter gene functionally linked downstream of the expression control region of the gene of this invention, (b) contacting a test sample with the cells, (c) detecting the activity of the reporter gene in the cells, and (d) selecting a compound that decreases or increases the activity compared with that in the case where the test sample is not contacted with the cells (control).

Herein, "functionally linked" means that the expression-controlling domain and a reporter gene are linked in such a way that the reporter gene linked to downstream of the expression-controlling domain can be expressed in response to the activation of the expression-controlling domain.

For example, after cloning the expression-controlling domain (promoter, enhancer, etc.) of the gene of this invention by screening a genomic DNA library with the nucleotide sequence set forth in SEQ ID NOs:1, 3 or 5 or portions thereof as the probe an expression vector is prepared to insert the domain to upstream of an appropriate reporter gene (chloramphenicol acetyltransferase gene, luciferase gene, etc.), and transferred to a mammalian cell line. Next, by contacting test samples with the cell line to detect the reporter activity, and selecting a compound to increase or decrease the reporter activity compared with that in the cells contacted with no test samples, compounds to suppress or promote the expression of the gene of this invention can be screened. Detecting the expression of the gene of this invention with the reporter activity as an index, this screening method is characteristic in its simplicity and easiness compared with the above-described direct detection method such as northern analysis.

These compounds that are isolated by screening and that promote or suppress the expression of the gene of this invention can be candidates of medicines for various disorders caused by the aberrant expression of the gene, and expected to be used as drugs to prevent or treat disorders such as cancer in particular. In addition, substances obtainable by using the above-described screening method, and having the structures of compounds to promote or suppress the gene expression of this invention which are partially modified by addition, deletion and/or substitution are also included in the compounds obtained by using the screening method of this invention.

When the compound obtained by the screening method of the invention is used as a pharmaceutical for humans and other mammals, such as, mice, rats, guinea pigs, rabbits, chicken, cats, dogs, sheep, pigs, bovines, monkeys, baboons, chimpanzees, the isolated compound can be administered not only directly, but also a dosage form using known pharmaceutical preparation methods. For example, according to the need, the drugs can be taken orally as sugarcoated tablets, capsules, elixirs and microcapsules or non-orally in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agent, surface-active agent, stabilizers, flavoring agents, excipients, vehicles, preservatives and binders, into a unit dose form required for generally accepted drug implementation. The amount of active ingredients in these preparations makes a suitable dosage within the indicated range acquirable.

Examples for additives which can be mixed to tablets and capsules are, binders such as gelatin, corn starch, tragacanth gum and gum acacia; excipients such as crystalline cellulose; swelling agents such as corn starch, gelatin and alginic acid; lubricants such as magnesium stearate; sweeteners such as sucrose, lactose or saccharin; flavoring agents such as peppermint, *Gaultheria adenothrix* oil and cherry. When the unit dosage form is a capsule, a liquid carrier such as oil can also be included in the above ingredients. Sterile composites for injections can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, and non-ionic surfactants such as Polysorbate 80 (TM) and HCO-50.

Sesame oil or Soy-bean oil can be used as a oleaginous liquid and may be used in conjunction with benzyl benzoate or benzyl alcohol as a solubilizers; may be formulated with a buffer such as phosphate buffer and sodium acetate buffer, a pain-killer such as procaine hydrochloride, a stabilizer such as benzyl alcohol and phenol, and an anti-oxidant. The prepared injection is filled into a suitable ampule.

Methods well known to one skilled in the art may be used to administer a pharmaceutical compound to patients, for example as intraarterial, intravenous, percutaneous injections and also as intranasal, transbronchial, intramuscular or oral administrations. The dosage varies according to the body-weight and age of a patient and the administration method, but one skilled in the art can suitably select them. If the compound can be encoded by a DNA, the DNA can be inserted into a vector for gene therapy and perform the therapy. The dosage and method of administration vary according to the body-weight, age, and symptoms of a patient, but one skilled in the art can select them suitably.

For example, although there are some differences according to the symptoms, the dose of a compound that binds with the transcriptional regulatory factor of the present invention and inhibits its activity is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally in the form of an injection to a normal adult (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kgs of body-weight.

All references and patents cited herein are incorporated by reference in their entirety.

EXAMPLES

In the following, the present invention will be more specifically described with reference to examples, but is not be construed as being limited thereto.

Example 1

Preparation of Subtractive Library of Fetal Gene

By the suppression subtractive hybridization method with cDNAs derived from fetal livers as the tester and cDNAs derived from adult livers as the driver, the subtraction method was performed to prepare a subtractive library comprising fetal genes expressed specifically or more prominently in the fetal liver.

A subtraction library was prepared using the PCR-Select™ cDNA Subtraction kit (CLONTECH) basically according to the method described by Luda Diatchenko et al. (Proc. Natl. Acad. Sci. USA, 93:6025–6030, 1996).

First, double-stranded cDNAs were synthesized from polyA$^+$ RNA prepared from human fetal (CLONTECH) and adult livers (CLONTECH) by the standard method using MMLV reverse transcriptase. Next, the respective cDNAs were blunt-ended with T4 DNA polymerase, and then cleaved by RsaI. A part of the cDNA originating from fetal liver (tester) was split in two; one of which was ligated with the adapter-1 and the other with the adapter-2. Each aliquot was mixed with 120-fold amount of the adult liver cDNA (driver), denatured by heat, and subjected to the first hybridization at 68° C. for 8 hours. Aliquots were then combined without heat denaturation, mixed further with an excess amount of heat-denatured driver, and subjected to the second hybridization at 68° C. for about 16 hours. The mixture was diluted with the dilution buffer, incubated at 75° C. for 7 minutes to remove the shorter strands of adapters, and used as a template for PCR. By performing PCR with primers corresponding to the adapters, PCR primers 1 and 2, cDNAs carrying different adapters on their two ends (subtracted cDNAs) were selectively amplified (suppression PCR). To obtain products with further selectivity, a portion of the amplified products was used as a template for PCR with primers Nested PCR primers 1 and 2, which locate further inside of the primers; PCR primers 1 and 2. The products were purified using the "QIAquick PCR Purification kit" (QIAGEN), and cloned into the pT7Blue-T vector (Novagen) by the TA cloning method to create a subtraction library.

Adaptors 1 and 2, primers 1 and 2, nested PCR primers 1 and 2 are shown in Table 1.

TABLE 1

```
Adaptor 1
5' CTAATACGACTCACTATAGGGCTCGAGCGGCCGCCCGGGCAGGT 3'    (SEQ ID NO:7)
                                  3'GGCCCGTCCA 5'    (SEQ ID NO:8)

Adaptor 2
5' TGTAGCGTGAAGACGACAGAAAGGGCGTGGTGCGGAGGGCGGT 3'    (SEQ ID NO:9)
                                  3'GCCTCCCGCCA 5'   (SEQ ID NO:10)

PCR primer 1
5' CTAATACGACTCACTATAGGGC 3'                          (SEQ ID NO:11)

PCR primer 2
5' TGTAGCGTGAAGACGACAGAA 3'                           (SEQ ID NO:12)

Nested PCR primer 1
5' TCGAGCGGCCGCCCGGGCAGGT 3'                          (SEQ ID NO:13)

Nested PCR primer 2
5' AGGGCGTGGTGCGGAGGGCGGT 3'                          (SEQ ID NO:14)
```

Example 2

Construction of Fetal Gene EST

By sequencing clones extracted from the library prepared in Example 1 at random, EST comprising fetal genes was constructed.

Plasmid DNA prepared by the alkali SDS method or products of colony PCR were used as a template for sequence reaction. Sequence reaction was performed by the cycle-sequencing method using the ABI PRISM™ Dye Terminator Cycle Sequencing Ready Reaction Kit With AmplyTaq DNA Polymerase, FS (Perkin Elmer), and the result was analyzed by the ABI 377 DNA Sequencer.

Colony PCR was performed as follows. Colonies carrying recombinant vectors were directly suspended into PCR reaction mixtures that contain vector primers, "M13 P4-22 primer" (5' CCAGGGTTTTCCCAGTCACGAC 3': SEQ ID NO:15) and "M13 P5-22 primer" (5' TCACACAGGAAA-CAGCTATGAC 3': SEQ ID NO:16). After PCR reaction, amplified insert DNA was separated from unreacted primers and nucleotides and such by gel filtration or the like, and used as a template for sequencing.

Example 3

RT-PCR Assay

As a result of EST (expressed sequence tags) construction by sequencing, primer sets specific for 84 kinds of ESTs having novel sequences were prepared respectively, and screening was performed to examine the expression of each gene in fetal liver, kidney, lung and brain as well as in adult liver, kidney, lung, brain, bone marrow and testis by RT-PCR.

Single-stranded cDNAs were synthesized from polyA$^+$ RNA (CLONTECH) or the total RNA by the standard method using a SUPERSCRIPT™ II RNase H$^-$ Reverse Transcriptase (GIBCO BRL), and a portion of the cDNAs thus obtained was used as the template for RT-PCR assay. PCR was carried out principally under the following conditions.

Composition of the reaction solution

TakaRa Taq (TaKaRa) 0.24 μl

TaqStart™ Antibody (CLONTECH) 0.24 μl

10×PCR buffer (TaKaRa) 3 μl 2.5 mM dNTPs (TaKaRa) 2.4 μl

20 μM primer 0.6 μl each

Template DNA 6 μl

/total volume 30 μl

Reaction conditions 1 cycle of 94° C. for 2 min; 28 to 35 cycles of 94° C. for 30 s, 50° C. to 60° C. for 1 min, and 72° C. for 1 min; and 1 cycle of 72° C. for 3 min.

Sixty-three clones that showed expression patterns specific in fetal tissues were selected, and then examined for their expressions in clinical samples of colon cancer and a variety of cancer cell strains. As a result, clones "fls353" and "fls485" were selected as the fetal genes with the expression activated in cancer cells.

Primer sets used in RT-PCR for amplifying "fls353" and "fls485", and G3PDH used as the control are shown in Table 2.

TABLE 2

```
fls353
FLS353 S1 primer 5' GATGCTTTCGTAGTTCAGATGTAA 3'    (SEQ ID NO:17)
FLS353 A1 primer 5' AATGCAGCAAGAGGTGGTGGAGAT 3'    (SEQ ID NO:18)

fls485
FLS485 S1 primer 5' GAGGGGGATCAGCTCAATGGTCTG 3'    (SEQ ID NO:19)
FLS485 A1 primer 5' ACCCCATCGTGGACTTCCCTCTGC 3'    (SEQ ID NO:20)

G3PDH
HG3 S1 primer    5' TCATCATCTCTGCCCCCTCTGCTG 3'    (SEQ ID NO:21)
HG3 A1 primer    5' GACGCCTGCTTCACCACCTTCTTG 3'    (SEQ ID NO:22)
```

Example 4

Cloning of Full Length cDNA of fls353

A 5'-stretch plus cDNA library derived from human fetal liver (CLONTECH) was screened by the plaque hybridization method with the fls353 original clone as the probe. Screening of about 5×10⁵ plaques resulted in gaining a few positive clones. DNA inserts of these positive clones were amplified by PCR and directly sequenced to determine their sequences. Public database search using the sequences thus obtained several ESTs which coincided with the 3'-terminus of fls353. Based on these EST sequences, FLS353 E2 primer (5'-CTGGTGCAGTTGGTGAGGTTTTCT 3'/SEQ ID NO:23) and FLS353 R1 primer (5'-CAATCACCGTCCCCAAGTCACCAG 3'/SEQ ID NO:24) were prepared, and the 3'-terminal fragments of fls353 gene were amplified by PCR with cDNA derived from human fetal liver as the template. Amplified fragments were subcloned into the pT7Blue-T vector (Novagen), and the nucleotide sequence of the 3'-terminal fragment containing a stop codon for fls353 gene was determined by sequencing a plurality of subclones. In addition, the 5'-terminus of fls353 gene was cloned by the 5' RACE (Rapid Amplification of cDNA Ends) method. That is, a 5'-terminal fragment (approximately 1.3 kbp) was amplified by PCR with a Marathon™ Ready cDNA (CLONTECH) as the template using the FLS353 S1 primer and AP1 primer (CLONTECH), and PCR products were subcloned into the pT7Blue-T vector. A plurality of subclones were sequenced to determine the nucleotide sequence of the 5'-terminus of fls353 gene containing the initiation codon.

cDNA containing the entire coding region was amplified from the fetal liver-derived cDNAs and such by PCR using FLS353 WN1 primer (5'-AGTCGCGGCCGCCGGTATG CAGAGAAGAGGACAGAA-3'/SEQ ID NO:25) and WN2 primer (5'-AGTCGCGGCCGCAAAAGGGGTGAAAGA GAAGATTGC-3'/SEQ ID NO:26).

Example 5

Cloning of Full-Length cDNA of fls485

Human testis cDNA library (CLONTECH) was plated on the plates by the standard method, and then transferred onto nylon membrane (Hybond N+). This membrane was cut into fragments presumed to contain about 200 plaques each, and the phage on the membrane was extracted into a lambda dilution buffer (SM). With the cDNA pool thus obtained as a template, screening was performed by PCR using the above-described FLS485 S1 primer and FLS485 A1 primer to identify a pool containing positive clones. With this pool as a template, a fragment (about 800 bp) of this positive clone was amplified using the above-described FLS485 A1 primer and GT10 S1 primer (5'-CTTTTGAGCAAGTTCAGCCT-3'/SEQ ID NO:27) which is a vector-primer of the library (λgt10 vector). After the sequence was confirmed, using this fragment as a probe, a human fetal liver-derived 5'-stretch plus cDNA library (CLONTECH) was screened by the plaque hybridization method. Screening of about 10⁶ plaques yielded 8 positive clones. DNA inserts of these positive clones were amplified by PCR and directly sequenced. Based on the sequence thus obtained, FLS485 A4 primer (5'-TTGAAATGTCCACTCGCTTATCCT-3'/SEQ ID NO:28) was prepared, and the 5'-terminal fragment was cloned by the 5' RACE (Rapid Amplification of cDNA Ends) method. A 5'-terminal fragment (approximately 600 bp) was amplified by PCR with a human fetal liver-derived Marathon™ Ready cDNA (CLONTECH) as a template using FLS485 A4 primer and AP1 primer (CLONTECH), and PCR-amplified products were subcloned into the pT7Blue-T vector (Novagen). A plurality of subclones was sequenced to determine the nucleotide sequence of the 5'-terminus of fls485 gene containing the initiation codon.

cDNA containing the entire coding region was amplified and cloned from the human fetal liver-derived cDNAs and such by PCR using a combination of the 5'-terminal sense primer and 3'-terminal antisense primer described in Table 3.

TABLE 3

```
5'-terminal sense primer
S1 primer
5' AGTCGCGGCCGCGCTAAGCAGGTGCGGAGGGGAGTC 3'    (SEQ ID NO:29)

S2 primer
5' AGTCGCGGCCGCCAGATATTCTTCCCACCTTTGGAG 3'    (SEQ ID NO:30)

3'-terminal antisense primer
A1 primer
5' AGTCGCGGCCGCGAGGAGCTGTATAAGGGGTTGGAG 3'    (SEQ ID NO:31)

A2 primer
5' AGTCGCGGCCGCTGCCAGGGTTTGTATGTGATTGTC 3'    (SEQ ID NO:32)
```

Example 6

Analyses of fls353

6-1 Expression Distribution in Normal Tissues

Expression distribution of fls353 in normal tissues was examined by northern analysis. The original clone of fls353 was labeled with [α-³²P]dCTP by the random primer method using the Ready-to Go DNA labeling beads (Pharmacia) to be used as a probe. Hybridization was performed at 68° C. in the ExpressHyb Hybridization Solution (CLONTECH) according to the method recommended by the manufacturer using the Multiple Tissue Northern (MTN) Blot□Human, Human II, Human III, Human Fetal II, Human Cancer Cell Line (CLONTECH). Final washing was performed in 0.1×SSC and 0.1% SDS at 50° C.

The results are shown in FIG. 1. Prominent expression of fls353 was detected in fetal liver, kidney, lung and brain, but almost no expression of it was seen in the corresponding adult tissues. Among other adult tissues, relatively strong expression was observed in thymus and testis, and only very weak expression was seen in other tissues.

6-2 Expression in Cancer Cell Strains

Figure 2:
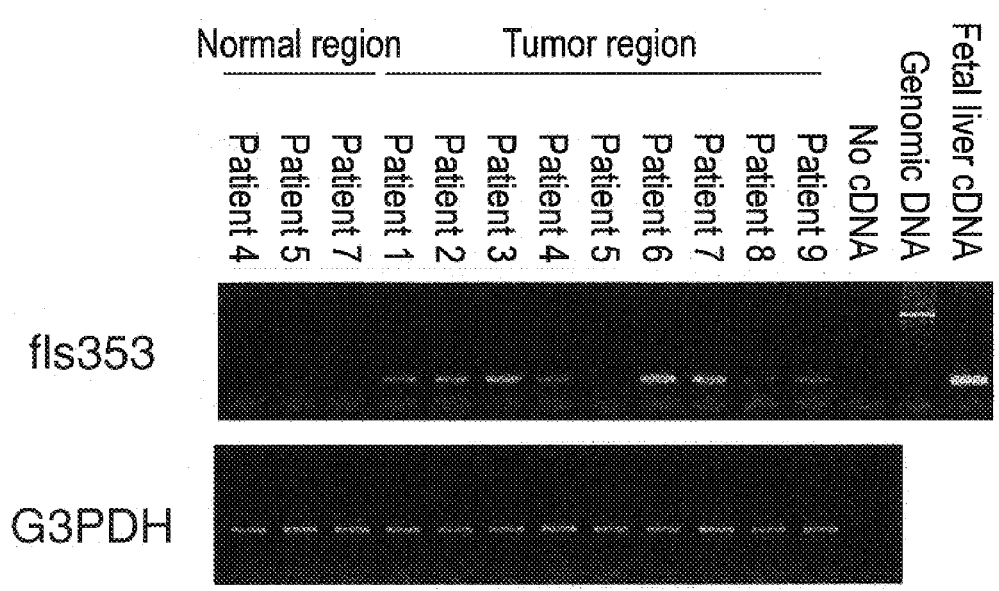
FIG. 2 is a photograph showing the results of the fls353 expression in a clinical sample of *E. coli*, analyzed by RT-PCR, continued to FIG. 3.
Figure 3:
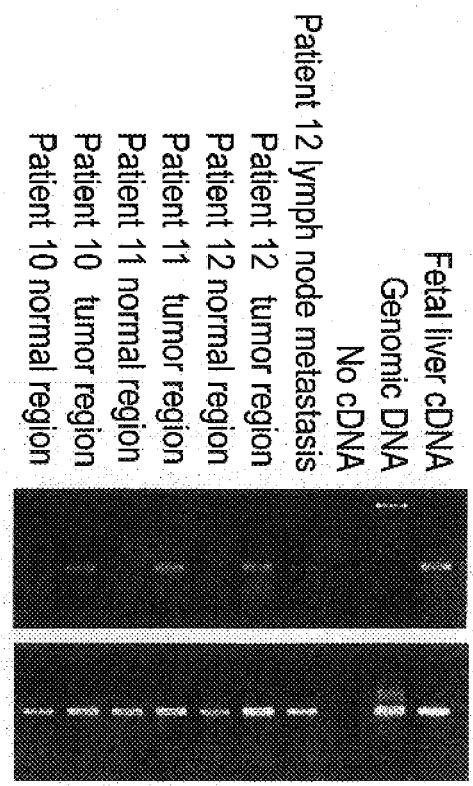
FIG. 3 is a photograph of the continuation of FIG. 2.

First, analyses of the fls353 expression in cancer cell strains similarly performed by the aforementioned northern hybridization detected its strong expression in 7 out of 8 cancer cell strains examined (FIG. 1). Subsequent examination of the fls353 expression in clinical samples of colon cancer by RT-PCR (FIGS. 2 and 3) resulted in the detection of its expression in 10 different types of tumors out of 12 types of samples. As the controls for 6 types out of these tumors, the fls353 expression was simultaneously examined in normal tissues taken from the same patient, but practically no expression was detected, indicating that the activation of fls353 expression is induced by malignant transformation of colon tissue cells.

6-3 Expression of fls353 in Clinical Cancer Samples

Figure 10:
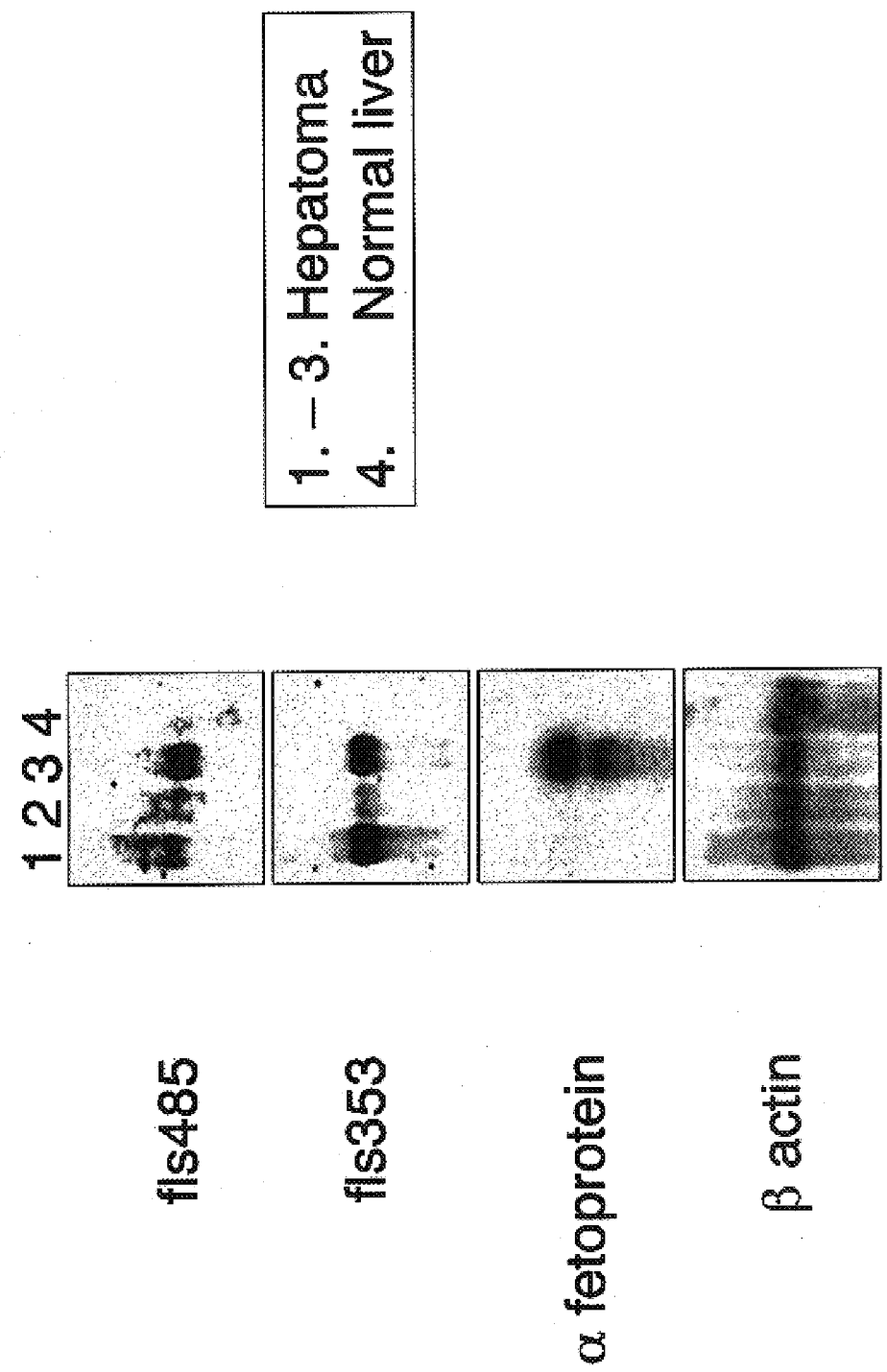
FIG. 10 is a photograph showing the results of northern blot analysis of the expressions of fls353, fls485 and a fetoprotein in a clinical hepatoma sample.
Figure 11:
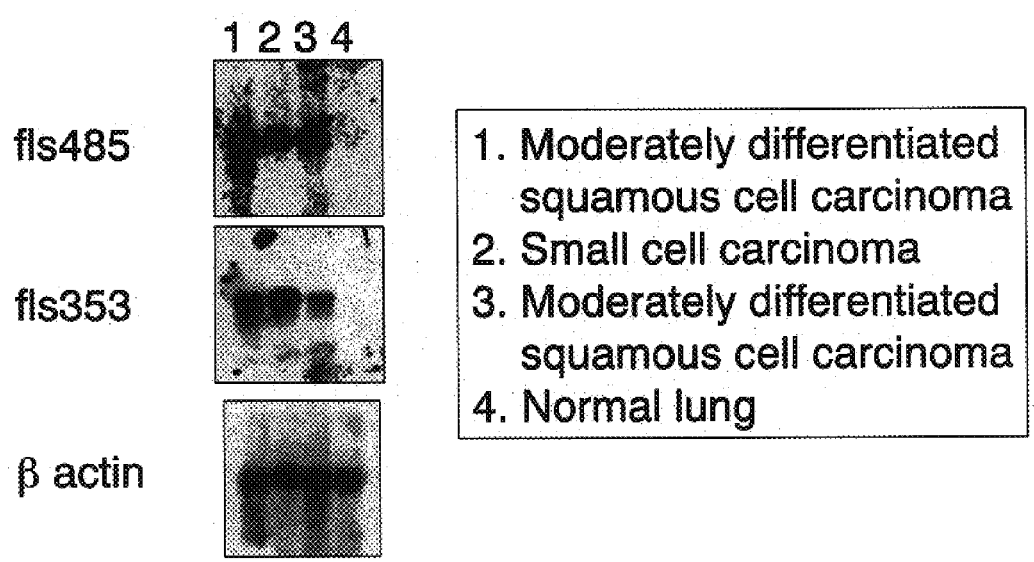
FIG. 11 is a photograph showing the results of northern analysis of the expressions of fls353 and fls485 in a clinical lung cancer sample.

Northern analysis of fls353 expression in clinical samples of hepatoma and lung cancer (FIGS. 10 and 11) resulted in a clear demonstration of its activated expression in cancer tissues. These results indicate that the fls353 expression is activated in a variety of cancer types, and involved in the progress of these cancers.

6-4 Structural Analyses cDNA covering the entire coding sequence of the fls353 gene was cloned by screening the cDNA library using the plaque hybridization method and RACE method and such, and sequenced. As a result, fls353 was proved to encode a protein comprising 747 amino acid residues (FIGS. 4 and 5). Nucleotide sequence of the fls353 cDNA thus determined and amino acid sequence encoded by the cDNA are shown in SEQ ID NOs:1 and 2, respectively. Database search using this amino acid sequence detected no protein showing a significant homology to the sequence. The fls353 protein is structurally characteristic in that it has the ATP/GTP binding consensus sequence (aa52–59, [Ala/Gly]-Xaa-Xaa-Xaa-Xaa-Gly-Lys-[Ser/Thr] (SEQ ID NO35), where Xaa represents any amino acid residue), and that its content percentage of basic amino acid, Lys, is high (13.2%), and assumed to be a basic protein (calculated isoelectric point pI=9.62). However, no motif predicting the function of this protein was detected.

Example 7

Analyses of fls485

7-1 Expression Distribution in Normal Tissues

Figure 6:
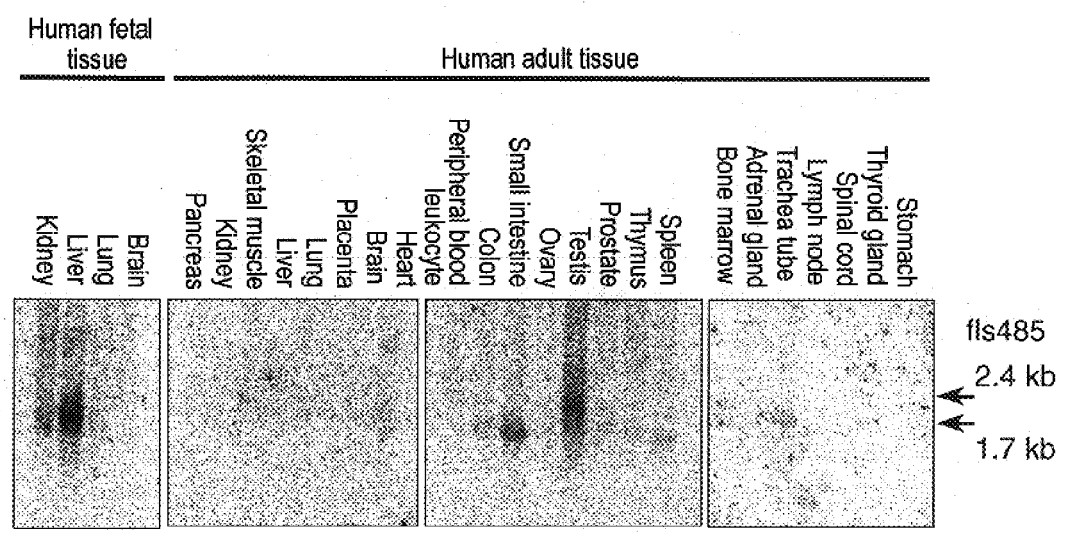
FIG. 6 is a photograph showing the results of the fls485 expression examined by northern blot analysis.

Expression of fls485 in normal tissues was examined by northern analysis (FIG. 6), which was performed similarly as the above-described fls353 using the original clones of fls485 as a probe.

As a result, it has been proved that fls485 is a gene which is expressed with an extremely high selectivity in organs such as fetal liver and kidney as well as adult testis and small intestine containing many undifferentiated cells, wherein cell differentiation and proliferation are actively in progress.

7-2 Expression in Tumor Cell Strains

Figure 7:
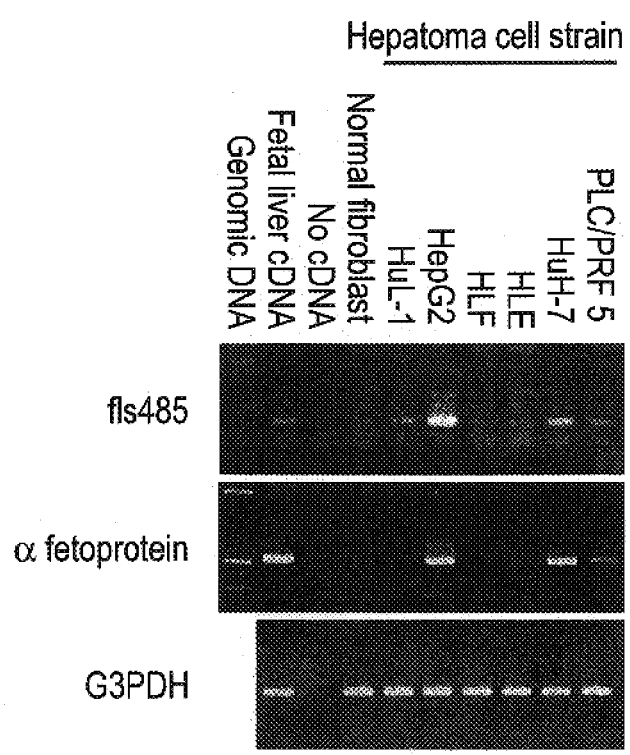
FIG. 7 is a photograph showing the results of RT-PCR analysis of the expression of fls485 and a fetoprotein in various cultured cells.

Examination of fls485 expression in cultured cells by RT-PCT analysis has revealed that fls485 exists in several hepatoma-derived cell strains—HepG2, HuH7 and PLC/PRF5 (Alexander), though not detected in primary culture of lung fibroblast which are normal cells (FIG. 7). Expression pattern of fls485 in hepatoma-derived cell strains coincided very well with that of α fetoprotein, a hepatoma tumor marker, indicating that a close correlation of fls485 expression with cell strains more reminiscent of the property of cancer cells in adult tissues. No expression of fls485 was detected in the adult liver at all on the analytical level either by northern analysis or even by the more sensitive RT-PCR analysis. These results indicate that fls485 expression is activated accompanied with a progress of malignant transformation of hepatocytes.

Also, the database search detected registration of four ESTs predicted to be derived from fls485 in a public database. Three out of these ESTs are derived from colon cancer cell strains (AA308814 and AA305159 are derived from the large intestine adenoma strain Caco2; AA622964 is derived from the colon cancer strain RER+). These results indicate the fls485 expression is also activated in certain types of colon cancers.

7-3 Expression in Clinical Cancer Samples

Northern analysis of fls485 expression in clinical samples of hepatoma and lung cancer (FIGS. 10 and 11) resulted in a clear demonstration of its activated expression in cancer tissues. These results indicate that the fls353 gene expression is activated in a variety of cancer types, and involved in the progress of these cancers.

7-4 Structural Analyses

Cloning of cDNA covering the entire coding region of fls485 has proved that the gene encodes a protein comprising 353 amino acid residues (FIG. 8). Nucleotide sequence of the full-length fls485 cDNA thus determined and the amino acid sequence encoded by the cDNA are shown in SEQ ID NOs:3 and 4, respectively. This amino acid sequence is characteristic as follows:

1. In the central portion, there exists a sequence predicted to be a zinc finger domain like C4-type. This domain is in the form of two repeats of a structural unit comprising two consecutive sequences each comprising Cys-Xaa-Xaa-Cys-Xaa-Gly-Xaa-Gly (SEQ ID NO:33) followed by one sequence comprising Cys-Xaa-Xaa-Cys-Xaa-Gly (SEQ ID NO:34).

2. The C-terminal sequence fits the consensus sequence of a Cys-Aaa-Aaa-Xaa (SEQ ID NO:36) box (Aaa mainly represents aliphatic amino acid). This motif is often observed in G-protein including ras proteins, and supposed to be a necessary motif for the mechanism to localize Cys to the inner side of cell membrane through its modification with lipids. No other signal for the intracellular localization is detected.

3. Furthermore, the C-terminal sequence also fits the (Ser/Thr)-Xaa-Val motif which is supposed to bind to a characteristic domain structure referred to as PDZ (DHR) domain which has been recently elucidated. This binding motif is observed in the binding of APC, a causative gene of familial polyposis, and human homologue of tumor suppressor gene DLG of *Drosophila*, which has been recognized as an important and principal binding motif in the intracellular signal transduction.

4. This protein is hydrophilic on the whole, and transmembrane domain, secretory signal, and such are not detected therein.

Homology search detected no protein having a significant homology to fls485 in database, although homology to several proteins was observed in the zinc finger-like domain.

Although the zinc finger domain is a structural domain often found in a large number of transcriptional regulatory factors, a zinc finger-like domain of fls485 is different from those of such a typical transcriptional regulatory factor type, and, furthermore, no sequence thought to be a nuclear transport signal has been detected in the fls485 amino acid sequence.

Figure 9:
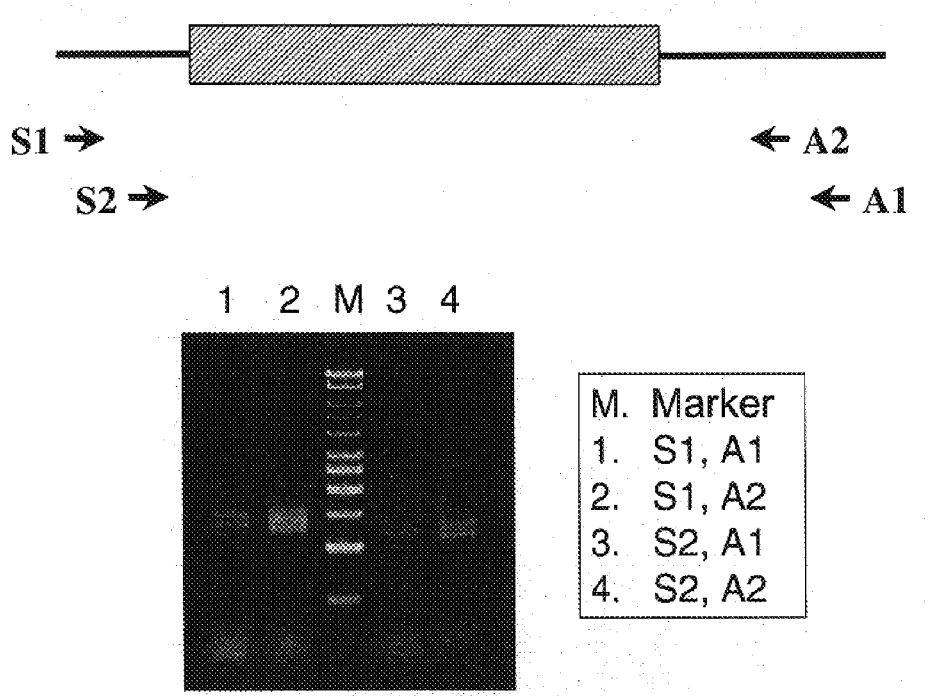
FIG. 9 is a photograph showing the results of RT-PCR using a set of primers sandwiching the entire coding region of fls485 with cDNA derived from the human fetal liver as the template. The shaded box in the above figure represents the coding regipn of fls485.

In addition, analysis by PCR has demonstrated the presence of two types of mRNAs for fls485, one comprising a sequence of 146 bp present in the 5'-terminus (fls485 L/SEQ ID NO:3) and the other skipping the sequence (fls485 S/SEQ ID NO:5) (FIG. 9). Since this region, underlined in FIG. 8, corresponds to the N-terminus of the putative coding region, fls485 L is able to encode a protein longer by 51 amino acids than fls485 S (amino acid sequence of fls485 L protein is shown in SEQ ID NO:4, and that of fls485 S protein in SEQ ID NO:6). Furthermore, northern analysis demonstrated the presence of a longer transcript in testis than those found in other tissues. However, analysis by PCR proved that this transcript has the same coding region as that in other tissues, and this was thought to be due to the difference in length in the 3'-untranslated region (UTR) (possibly due to the difference in the polyA addition site).

INDUSTRIAL APPLICABILITY

The present invention has provided novel proteins which are specifically or more prominently expressed in fetal tissues, and genes encoding the proteins. The genes are strongly expressed in tumor cells, and assumed to participate in malignant transformation of cells. Therefore, expression inhibitors for fetal genes of this invention are expected to be useful as antitumor agents. Furthermore, it is possible to utilize the fetal genes of this invention and proteins encoded by the genes as the tool for purification and cloning of novel factors involved in cell proliferation, immortalization, cellular infiltration, metastasis and angiogenesis, and further as the tool for the development of drugs for various disorders caused by the aberrant activation of gene expression of this invention due to the irregularity of expression control in vivo. It is thought it possible to develop medicines depending on novel action mechanisms by designing drugs targeted on the genes of this invention.

What is claimed is:

1. An isolated nucleic acid encoding a protein comprising the amino acid sequence of SEQ ID NO:2.

2. An isolated nucleic acid encoding a polypeptide, the amino acid sequence of which consists of SEQ ID NO:2.

3. An isolated nucleic acid comprising the coding region of SEQ ID NO:1.

4. A vector into which the nucleic acid of claim 1 is inserted.

5. A vector into which the nucleic acid of claim 2 is inserted.

6. A vector comprising the nucleic acid of claim 3.

7. A transformant harboring the nucleic acid of claim 1.

8. A transformant harboring the nucleic acid of claim 2.

9. A transformant harboring the vector of claim 4.

10. A transformant harboring the vector of claim 5.

11. A transformant harboring the nucleic acid of claim 3.

12. A transformant harboring the vector of claim 6.

13. A method for producing a polypeptide, the method comprising the steps of culturing the transformant of claim 7 and recovering the polypeptide from the transformant or the culture supernatant thereof.

14. A method for producing a polypeptide, the method comprising the steps of culturing the transformant of claim 8 and recovering the polypeptide from the transformant or the culture supernatant thereof.

15. A method for producing a polypeptide, the method comprising the steps of culturing the transformant of claim 11 and recovering the polypeptide encoded by the nucleic acid from the transformant or the culture supernatant thereof.

16. A method for screening for a compound that suppresses or promotes expression of a nucleic acid according to claim 1, the method comprising:
   (a) contacting cells expressing the nucleic acid with a test compound,
   (b) detecting expression of the nucleic acid in the cells in the presence of the test compound by hybridization with a probe that is a nucleic acid according to claim 1, and
   (c) identifying a compound that decreases or increases expression of the nucleic acid compared with expression of the nucleic acid in the absence of the test compound.

17. A method for screening for a compound that suppresses or promotes expression of a nucleic acid according to claim 2, the method comprising:
   (a) contacting cells expressing the nucleic acid with a test compound,
   (b) detecting expression of the nucleic acid in the cells in the presence of the test compound by hybridization with a probe that is a nucleic acid according to claim 2, and
   (c) identifying a compound that decreases or increases expression of the nucleic acid compared with expression of the nucleic acid in the absence of the test compound.

18. A method for screening for a compound that suppresses or promotes expression of a nucleic acid according to claim 3, the method comprising:
   (a) contacting cells expressing the nucleic acid with a test compound,
   (b) detecting expression of the nucleic acid in the cells in the presence of the test compound by hybridization with a probe that is a nucleic acid according to claim 3, and
   (c) identifying a compound that decreases or increases expression of the nucleic acid compared with expression of the nucleic acid in the absence of the test compound.

19. A method for screening for a compound that suppresses or promotes expression of a nucleic acid encoding a protein comprising the amino acid sequence of SEQ ID NO:2, said method comprising:
   (a) contacting the transformant of claim 7 with a test compound,
   (b) detecting expression of the nucleic acid in the transformant in the presence of the test compound, and
   (c) identifying a compound that decreases or increases expression of the nucleic acid, compared with expression of the nucleic acid in the absence of the test compound.

20. A method for screening for a compound that suppresses or promotes expression of a nucleic acid encoding a polypeptide, of which the amino acid sequence consists of SEQ ID NO:2, said method comprising:
   (a) contacting the transformant of claim 8 with a test compound,
   (b) detecting expression of the nucleic acid in the transformant in the presence of the test compound, and
   (c) identifying a compound that decreases or increases expression of the nucleic acid, compared with expression of the nucleic acid in the absence of the test compound.

21. A method for screening for a compound that suppresses or promotes expression of a nucleic acid that comprises the coding region of SEQ ID NO:1, said method comprising:
   (a) contacting the transformant of claim 11 with a test compound,
   (b) detecting expression of the nucleic acid in the transformant in the presence of the test compound, and
   (c) identifying a compound that decreases or increases expression of the nucleic acid, compared with expression of the nucleic acid in the absence of the test compound.

* * * * *

SEQUENCE LISTING

```
<160> NUMBER OF SEQ ID NOS: 36

<210> SEQ ID NO 1
<211> LENGTH: 3403
<212> TYPE: DNA
<213> ORGANISM: Homo sapiens
<220> FEATURE:
<221> NAME/KEY: CDS
<222> LOCATION: (472)...(2712)

<400> SEQUENCE: 1
caggtctgag gcgaagctag gtgagccgtg ggaagaaaag agggagcagc tagggcgcgg      60
gtctccctcc tcccggagtt tggaacggct gaagttcacc ttccagcccc tagcgccgtt     120
cgcgccgcta ggcctggctt ctgaggcggt tgcggtgctc ggtcgccgcc taagcggggc     180
agggtgcgaa caggggcttc gggccacgct tctcttggcg acaggatttt gctgtgaagt     240
ccgtccggga aacggaggaa aaaagagtt gcgggaggct gtctgctaat aacggttctt      300
gatacatatt tgccagactt caagatttca gaaaaggggt gaaagagaag attgcaactt     360
tgagtcagac ctgtaggcct gatagactga ttaaaccaca gaaggtgacc tgctgagaaa     420
agtggtacaa atactgggaa aaacctgctc ttctgcgtta agtgggagac a atg tca     477
                                                                 Met Ser
                                                                  1 caa gtt aaa agc tct tat tcc tat gat gcc ccc tcg gat ttc atc aat    525
Gln Val Lys Ser Ser Tyr Ser Tyr Asp Ala Pro Ser Asp Phe Ile Asn
      5                  10                  15 ttt tca tcc ttg gat gat gaa gga gat act caa aac ata gat tca tgg    573
Phe Ser Ser Leu Asp Asp Glu Gly Asp Thr Gln Asn Ile Asp Ser Trp
 20                  25                  30 ttt gag gag aag gcc aat ttg gag aat aag tta ctg ggg aag aat gga    621
Phe Glu Glu Lys Ala Asn Leu Glu Asn Lys Leu Leu Gly Lys Asn Gly
 35                  40                  45                  50 act gga ggg ctt ttt cag ggc aaa act cct ttg aga aag gct aat ctt    669
Thr Gly Gly Leu Phe Gln Gly Lys Thr Pro Leu Arg Lys Ala Asn Leu
                 55                  60                  65 cag caa gct att gtc aca cct ttg aaa cca gtt gac aac act tac tac    717
Gln Gln Ala Ile Val Thr Pro Leu Lys Pro Val Asp Asn Thr Tyr Tyr
             70                  75                  80 aaa gag gca gaa aaa gaa aat ctt gtg gaa caa tcc att ccg tca aat    765
Lys Glu Ala Glu Lys Glu Asn Leu Val Glu Gln Ser Ile Pro Ser Asn
         85                  90                  95 gct tgt tct tcc ctg gaa gtt gag gca gcc ata tca aga aaa act cca    813
Ala Cys Ser Ser Leu Glu Val Glu Ala Ala Ile Ser Arg Lys Thr Pro
    100                 105                 110 gcc cag cct cag aga aga tct ctt agg ctt tct gct cag aag gat ttg    861
```

-continued

| | | |
|---|---|---|
| Ala Gln Pro Gln Arg Arg Ser Leu Arg Leu Ser Ala Gln Lys Asp Leu<br>115                    120                    125                   130 | |
| gaa cag aaa gaa aag cat cat gta aaa atg aaa gcc aag aga tgt gcc<br>Glu Gln Lys Glu Lys His His Val Lys Met Lys Ala Lys Arg Cys Ala<br>                       135                   140                 145 | 909 |
| act cct gta atc atc gat gaa att cta ccc tct aag aaa atg aaa gtt<br>Thr Pro Val Ile Ile Asp Glu Ile Leu Pro Ser Lys Lys Met Lys Val<br>        150                   155                   160 | 957 |
| tct aac aac aaa aag aag cca gag gaa gaa ggc agt gct cat caa gat<br>Ser Asn Asn Lys Lys Lys Pro Glu Glu Glu Gly Ser Ala His Gln Asp<br>             165                  170               175 | 1005 |
| act gct gaa aac aat gca tct tcc cca gag aaa gcc aag ggt aga cat<br>Thr Ala Glu Asn Asn Ala Ser Ser Pro Glu Lys Ala Lys Gly Arg His<br>180                    185                    190 | 1053 |
| act gtg cct tgt atg cca cct gca aag cag aag ttt cta aaa agt act<br>Thr Val Pro Cys Met Pro Pro Ala Lys Gln Lys Phe Leu Lys Ser Thr<br>195                    200                   205                 210 | 1101 |
| gag gag caa gag ctg gag aag agt atg aaa atg cag caa gag gtg gtg<br>Glu Glu Gln Glu Leu Glu Lys Ser Met Lys Met Gln Gln Glu Val Val<br>                    215                   220               225 | 1149 |
| gag atg cgg aaa aag aat gaa gaa ttc aag aaa ctt gct ctg gct gga<br>Glu Met Arg Lys Lys Asn Glu Glu Phe Lys Lys Leu Ala Leu Ala Gly<br>            230                   235                 240 | 1197 |
| ata ggg caa cct gtg aag aaa tca gtg agc cag gtc acc aaa tca gtt<br>Ile Gly Gln Pro Val Lys Lys Ser Val Ser Gln Val Thr Lys Ser Val<br>              245                  250               255 | 1245 |
| gac ttc cac ttc cgc aca gat gag cga atc aaa caa cat cct aag aac<br>Asp Phe His Phe Arg Thr Asp Glu Arg Ile Lys Gln His Pro Lys Asn<br>260                    265                   270 | 1293 |
| cag gag gaa tat aag gaa gtg aac ttt aca tct gaa cta cga aag cat<br>Gln Glu Glu Tyr Lys Glu Val Asn Phe Thr Ser Glu Leu Arg Lys His<br>275                    280                   285               290 | 1341 |
| cct tca tct cct gcc cga gtg act aag gga tgt acc att gtt aag cct<br>Pro Ser Ser Pro Ala Arg Val Thr Lys Gly Cys Thr Ile Val Lys Pro<br>                    295                   300               305 | 1389 |
| ttc aac ctg tcc caa gga aag aaa aga aca ttt gat gaa aca gtt tct<br>Phe Asn Leu Ser Gln Gly Lys Lys Arg Thr Phe Asp Glu Thr Val Ser<br>            310                   315                 320 | 1437 |
| aca tat gtg ccc ctt gca cag caa gtt gaa gac ttc cat aaa cga acc<br>Thr Tyr Val Pro Leu Ala Gln Gln Val Glu Asp Phe His Lys Arg Thr<br>              325                  330               335 | 1485 |
| cct aac aga tat cat ttg agg agc aag aag gat gat att aac ctg tta<br>Pro Asn Arg Tyr His Leu Arg Ser Lys Lys Asp Asp Ile Asn Leu Leu<br>340                    345                   350 | 1533 |
| ccc tcc aaa tct tct gtg acc aag att tgc aga gac cca cag act cct<br>Pro Ser Lys Ser Ser Val Thr Lys Ile Cys Arg Asp Pro Gln Thr Pro<br>355                    360                   365               370 | 1581 |
| gta ctg caa acc aaa cac cgt gca cgg gct gtg acc tgc aaa agt aca<br>Val Leu Gln Thr Lys His Arg Ala Arg Ala Val Thr Cys Lys Ser Thr<br>                  375                   380               385 | 1629 |
| gca gag ctg gag gct gag gag ctc gag aaa ttg caa caa tac aaa ttc<br>Ala Glu Leu Glu Ala Glu Glu Leu Glu Lys Leu Gln Gln Tyr Lys Phe<br>                    390                   395               400 | 1677 |
| aaa gca cgt gaa ctt gat ccc aga ata ctt gaa ggt ggg ccc atc ttg<br>Lys Ala Arg Glu Leu Asp Pro Arg Ile Leu Glu Gly Gly Pro Ile Leu<br>405                    410                   415 | 1725 |
| ccc aag aaa cca cct gtg aaa cca ccc acc gag cct att ggc ttt gat<br>Pro Lys Lys Pro Pro Val Lys Pro Pro Thr Glu Pro Ile Gly Phe Asp<br>420                    425                   430 | 1773 |

```
ttg gaa att gag aaa aga atc cag gag cga gaa tca aag aag aaa aca      1821
Leu Glu Ile Glu Lys Arg Ile Gln Glu Arg Glu Ser Lys Lys Lys Thr
435                 440                 445                 450 gag gat gaa cac ttt gaa ttt cat tcc aga cct tgc cct act aag att      1869
Glu Asp Glu His Phe Glu Phe His Ser Arg Pro Cys Pro Thr Lys Ile
            455                 460                 465 ttg gaa gat gtt gtg ggt gtt cct gaa aag aag gta ctt cca atc acc      1917
Leu Glu Asp Val Val Gly Val Pro Glu Lys Lys Val Leu Pro Ile Thr
                470                 475                 480 gtc ccc aag tca cca gcc ttt gca ttg aag aac aga att cga atg ccc      1965
Val Pro Lys Ser Pro Ala Phe Ala Leu Lys Asn Arg Ile Arg Met Pro
            485                 490                 495 acc aaa gaa gat gag gaa gag gac gaa ccg gta gtg ata aaa gct caa      2013
Thr Lys Glu Asp Glu Glu Glu Asp Glu Pro Val Val Ile Lys Ala Gln
500                 505                 510 cct gtg cca cat tat ggg gtg cct ttt aag ccc caa atc cca gag gca      2061
Pro Val Pro His Tyr Gly Val Pro Phe Lys Pro Gln Ile Pro Glu Ala
515                 520                 525                 530 aga act gtg gaa ata tgc cct ttc tcg ttt gat tct cga gac aaa gaa      2109
Arg Thr Val Glu Ile Cys Pro Phe Ser Phe Asp Ser Arg Asp Lys Glu
                535                 540                 545 cgt cag tta cag aag gag aag aaa ata aaa gaa ctg cag aaa ggg gag      2157
Arg Gln Leu Gln Lys Glu Lys Lys Ile Lys Glu Leu Gln Lys Gly Glu
            550                 555                 560 gtg ccc aag ttc aag gca ctt ccc ttg cct cat ttt gac acc att aac      2205
Val Pro Lys Phe Lys Ala Leu Pro Leu Pro His Phe Asp Thr Ile Asn
                565                 570                 575 ctg cca gag aag aag gta aag aat gtg acc cag att gaa cct ttc tgc      2253
Leu Pro Glu Lys Lys Val Lys Asn Val Thr Gln Ile Glu Pro Phe Cys
580                 585                 590 ttg gag act gac aga aga ggt gct ctg aag gca cag act tgg aag cac      2301
Leu Glu Thr Asp Arg Arg Gly Ala Leu Lys Ala Gln Thr Trp Lys His
595                 600                 605                 610 cag ctg gaa gaa gaa ctg aga cag cag aaa gaa gca gct tgt ttc aag      2349
Gln Leu Glu Glu Glu Leu Arg Gln Gln Lys Glu Ala Ala Cys Phe Lys
                615                 620                 625 gct cgt cca aac acc gtc atc tct cag gag ccc ttt gtt ccc aag aaa      2397
Ala Arg Pro Asn Thr Val Ile Ser Gln Glu Pro Phe Val Pro Lys Lys
            630                 635                 640 gag aag aaa tca gtt gct gag ggc ctt tct ggt tct cta gtt cag gaa      2445
Glu Lys Lys Ser Val Ala Glu Gly Leu Ser Gly Ser Leu Val Gln Glu
                645                 650                 655 cct ttt cag ctg gct act gag aag aga gcc aaa gag cgg cag gag ctg      2493
Pro Phe Gln Leu Ala Thr Glu Lys Arg Ala Lys Glu Arg Gln Glu Leu
660                 665                 670 gag aag aga atg gct gag gta gaa gcc cag aaa gcc cag cag ttg gag      2541
Glu Lys Arg Met Ala Glu Val Glu Ala Gln Lys Ala Gln Gln Leu Glu
675                 680                 685                 690 gag gcc aga cta cag gag gaa gag cag aaa aaa gag gag ctg gcc agg      2589
Glu Ala Arg Leu Gln Glu Glu Glu Gln Lys Lys Glu Glu Leu Ala Arg
                695                 700                 705 cta cgg aga gaa ctg gtg cat aag gca aat cca ata cgc aag tac cag      2637
Leu Arg Arg Glu Leu Val His Lys Ala Asn Pro Ile Arg Lys Tyr Gln
            710                 715                 720 ggt ctg gag ata aag tca agt gac cag cct ctg act gtg cct gta tct      2685
Gly Leu Glu Ile Lys Ser Ser Asp Gln Pro Leu Thr Val Pro Val Ser
                725                 730                 735 ccc aaa ttc tcc act cga ttc cac tgc taaactcagc tgtgagctgc           2732
Pro Lys Phe Ser Thr Arg Phe His Cys
            740                 745
```

-continued

```
ggataccgcc cggcaatggg acctgctctt aacctcaaac ctaggaccgt cttgctttgt    2792
cattgggcat ggagagaacc catttctcca gacttttacc tacccgtgcc tgagaaagca    2852
tacttgacaa ctgtggactc cagttttgtt gagaattgtt ttcttacatt actaaggcta    2912
ataatgagat gtaactcatg aatgtctcga ttagactcca tgtagttact tcctttaaac    2972
catcagccgg cctttatat gggtcttcac tctgactaga atttagtctc tgtgtcagca     3032
cagtgtaatc tctattgcta ttgccccta cgactctcac cctctcccca cttttttta     3092 aaattttaac cagaaaataa agatagttaa atcctaagat agagattaag tcatggttta    3152
aatgaggaac aatcagtaaa tcagattctg tcctcttctc tgcataccgt gaatttatag    3212
ttaaggatcc ctttgctgtg agggtagaaa acctcaccaa ctgcaccagt gaggaagaag    3272
actgcgtgga ttcatgggga gcctcacagc agccacgcag caggctctgg gtggggctgc    3332
cgttaaggca cagttctttc cttactggtg ctgataacaa cagggaaccg tgcagtgtgc    3392
attttaagac c                                                        3403
```

<210> SEQ ID NO 2
<211> LENGTH: 747
<212> TYPE: PRT
<213> ORGANISM: Homo sapiens

<400> SEQUENCE: 2

```
Met Ser Gln Val Lys Ser Ser Tyr Ser Tyr Asp Ala Pro Ser Asp Phe
 1               5                  10                  15

Ile Asn Phe Ser Ser Leu Asp Asp Glu Gly Asp Thr Gln Asn Ile Asp
                20                  25                  30

Ser Trp Phe Glu Glu Lys Ala Asn Leu Glu Asn Lys Leu Leu Gly Lys
            35                  40                  45

Asn Gly Thr Gly Gly Leu Phe Gln Gly Lys Thr Pro Leu Arg Lys Ala
        50                  55                  60

Asn Leu Gln Gln Ala Ile Val Thr Pro Leu Lys Pro Val Asp Asn Thr
65                  70                  75                  80

Tyr Tyr Lys Glu Ala Glu Lys Glu Asn Leu Val Glu Gln Ser Ile Pro
                85                  90                  95

Ser Asn Ala Cys Ser Ser Leu Glu Val Glu Ala Ala Ile Ser Arg Lys
            100                 105                 110

Thr Pro Ala Gln Pro Gln Arg Arg Ser Leu Arg Leu Ser Ala Gln Lys
        115                 120                 125

Asp Leu Glu Gln Lys Glu Lys His His Val Lys Met Lys Ala Lys Arg
    130                 135                 140

Cys Ala Thr Pro Val Ile Ile Asp Glu Ile Leu Pro Ser Lys Lys Met
145                 150                 155                 160

Lys Val Ser Asn Asn Lys Lys Pro Glu Glu Glu Gly Ser Ala His
                165                 170                 175

Gln Asp Thr Ala Glu Asn Asn Ala Ser Ser Pro Glu Lys Ala Lys Gly
            180                 185                 190

Arg His Thr Val Pro Cys Met Pro Pro Ala Lys Gln Lys Phe Leu Lys
        195                 200                 205

Ser Thr Glu Glu Gln Glu Leu Glu Lys Ser Met Lys Met Gln Gln Glu
    210                 215                 220

Val Val Glu Met Arg Lys Lys Asn Glu Glu Phe Lys Lys Leu Ala Leu
225                 230                 235                 240

Ala Gly Ile Gly Gln Pro Val Lys Lys Ser Val Ser Gln Val Thr Lys
```

-continued

```
            245                 250                 255
Ser Val Asp Phe His Phe Arg Thr Asp Glu Arg Ile Lys Gln His Pro
        260                 265                 270
Lys Asn Gln Glu Glu Tyr Lys Glu Val Asn Phe Thr Ser Glu Leu Arg
        275                 280                 285
Lys His Pro Ser Ser Pro Ala Arg Val Thr Lys Gly Cys Thr Ile Val
        290                 295                 300
Lys Pro Phe Asn Leu Ser Gln Gly Lys Lys Arg Thr Phe Asp Glu Thr
305                 310                 315                 320
Val Ser Thr Tyr Val Pro Leu Ala Gln Val Glu Asp Phe His Lys
                325                 330                 335
Arg Thr Pro Asn Arg Tyr His Leu Arg Ser Lys Lys Asp Asp Ile Asn
        340                 345                 350
Leu Leu Pro Ser Lys Ser Ser Val Thr Lys Ile Cys Arg Asp Pro Gln
        355                 360                 365
Thr Pro Val Leu Gln Thr Lys His Arg Ala Arg Ala Val Thr Cys Lys
        370                 375                 380
Ser Thr Ala Glu Leu Glu Ala Glu Leu Glu Lys Leu Gln Gln Tyr
385                 390                 395                 400
Lys Phe Lys Ala Arg Glu Leu Asp Pro Arg Ile Leu Glu Gly Gly Pro
                405                 410                 415
Ile Leu Pro Lys Lys Pro Val Lys Pro Pro Thr Glu Pro Ile Gly
        420                 425                 430
Phe Asp Leu Glu Ile Glu Lys Arg Ile Gln Glu Arg Glu Ser Lys Lys
        435                 440                 445
Lys Thr Glu Asp Glu His Phe Glu Phe His Ser Arg Pro Cys Pro Thr
450                 455                 460
Lys Ile Leu Glu Asp Val Val Gly Val Pro Glu Lys Lys Val Leu Pro
465                 470                 475                 480
Ile Thr Val Pro Lys Ser Pro Ala Phe Ala Leu Lys Asn Arg Ile Arg
                485                 490                 495
Met Pro Thr Lys Glu Asp Glu Glu Asp Glu Pro Val Val Ile Lys
                500                 505                 510
Ala Gln Pro Val Pro His Tyr Gly Val Pro Phe Lys Pro Gln Ile Pro
        515                 520                 525
Glu Ala Arg Thr Val Glu Ile Cys Pro Phe Ser Phe Asp Ser Arg Asp
        530                 535                 540
Lys Glu Arg Gln Leu Gln Lys Glu Lys Lys Ile Lys Glu Leu Gln Lys
545                 550                 555                 560
Gly Glu Val Pro Lys Phe Lys Ala Leu Pro Leu Pro His Phe Asp Thr
                565                 570                 575
Ile Asn Leu Pro Glu Lys Lys Val Lys Asn Val Thr Gln Ile Glu Pro
                580                 585                 590
Phe Cys Leu Glu Thr Asp Arg Arg Gly Ala Leu Lys Ala Gln Thr Trp
        595                 600                 605
Lys His Gln Leu Glu Glu Glu Leu Arg Gln Gln Lys Glu Ala Ala Cys
        610                 615                 620
Phe Lys Ala Arg Pro Asn Thr Val Ile Ser Gln Glu Pro Phe Val Pro
625                 630                 635                 640
Lys Lys Glu Lys Lys Ser Val Ala Glu Gly Leu Ser Gly Ser Leu Val
                645                 650                 655
Gln Glu Pro Phe Gln Leu Ala Thr Glu Lys Arg Ala Lys Glu Arg Gln
        660                 665                 670
```

-continued

```
Glu Leu Glu Lys Arg Met Ala Glu Val Glu Ala Gln Lys Ala Gln Gln
            675                 680                 685

Leu Glu Glu Ala Arg Leu Gln Glu Glu Gln Lys Lys Glu Glu Leu
        690                 695                 700

Ala Arg Leu Arg Arg Glu Leu Val His Lys Ala Asn Pro Ile Arg Lys
705                 710                 715                 720

Tyr Gln Gly Leu Glu Ile Lys Ser Ser Asp Gln Pro Leu Thr Val Pro
                    725                 730                 735

Val Ser Pro Lys Phe Ser Thr Arg Phe His Cys
            740                 745
```

<210> SEQ ID NO 3
<211> LENGTH: 1545
<212> TYPE: DNA
<213> ORGANISM: Homo sapiens
<220> FEATURE:
<221> NAME/KEY: CDS
<222> LOCATION: (247)...(1305)

<400> SEQUENCE: 3

```
ctcacactgg ctggcactgc taagcaggtg cggaggggag tcagagaccc ccggatggag      60
gggtgtggtg gacctcagtt ttgaggccga gagtcctctg gcgccccca cagagctcct     120 ggagagactg cccagctatg actggcttct tcaaggggc agaggacaga tattcttccc     180
acctttggag gccccaggga ggccccagga gcaaaggtcc tggccctcgt tcctggaaca     240 caggag atg ccc tcc cca gtt gga ctg ctg agg gct tta cca cta ccg       288
       Met Pro Ser Pro Val Gly Leu Leu Arg Ala Leu Pro Leu Pro
         1               5                  10 tgg cct cag ttt ctc gcc tgc acg ttg agg agg ctg gct ggc cgc gt       336
Trp Pro Gln Phe Leu Ala Cys Thr Leu Arg Arg Leu Ala Gly Pro Arg
 15                  20                  25                  30 gag tcc aca ggc cct tcc cag aag ccc ccg cct ctc tgt tcg gtc ccc      384
Glu Ser Thr Gly Pro Ser Gln Lys Pro Pro Pro Leu Cys Ser Val Pro
                 35                  40                  45 tgc aga gtc cct gcg atg acg gag gag gtg gcc cgg gaa gcc ctc ctc      432
Cys Arg Val Pro Ala Met Thr Glu Glu Val Ala Arg Glu Ala Leu Leu
             50                  55                  60 agc ttt gtg gac tct aag tgc tgc tac agc agc acg gtg gct gga gac      480
Ser Phe Val Asp Ser Lys Cys Cys Tyr Ser Ser Thr Val Ala Gly Asp
         65                  70                  75 ctc gtc atc cag gag ctg aag cgg cag acc ctc tgc agg tac cgt ctg      528
Leu Val Ile Gln Glu Leu Lys Arg Gln Thr Leu Cys Arg Tyr Arg Leu
     80                  85                  90 gag acc ttt agt gaa tcc agg ata agc gag tgg aca ttt caa ccc ttt      576
Glu Thr Phe Ser Glu Ser Arg Ile Ser Glu Trp Thr Phe Gln Pro Phe
 95                 100                 105                 110 act aac cac tct gtg gat ggg ccg caa aga ggc gcc tcc ccc agg ctc      624
Thr Asn His Ser Val Asp Gly Pro Gln Arg Gly Ala Ser Pro Arg Leu
                115                 120                 125 tgg gac atc aag gtt caa ggt cct ccg atg ttt cag gaa gac acc agg      672
Trp Asp Ile Lys Val Gln Gly Pro Pro Met Phe Gln Glu Asp Thr Arg
            130                 135                 140 aag ttc cag gtc cct cac tcg tca ctg gtc aag gaa tgc cac aaa tgc      720
Lys Phe Gln Val Pro His Ser Ser Leu Val Lys Glu Cys His Lys Cys
        145                 150                 155 cat ggg cgt ggg cgg tac aag tgc agc ggc tgc cac ggg gcg ggc acg      768
His Gly Arg Gly Arg Tyr Lys Cys Ser Gly Cys His Gly Ala Gly Thr
    160                 165                 170
```

| | | |
|---|---|---|
| gtg cgg tgc cca tcc tgc tgc gga gcc aag cgc aaa gcc aag cag tcc<br>Val Arg Cys Pro Ser Cys Cys Gly Ala Lys Arg Lys Ala Lys Gln Ser<br>175                    180                  185                190 | | 816 |
| cgg aga tgt cag ctg tgc gcg ggg tcc ggc agg cga aga tgc agc act<br>Arg Arg Cys Gln Leu Cys Ala Gly Ser Gly Arg Arg Arg Cys Ser Thr<br>                  195                  200                205 | | 864 |
| tgc tca ggg aga ggg aac aag acc tgc gcc acc tgc aag ggg gag aag<br>Cys Ser Gly Arg Gly Asn Lys Thr Cys Ala Thr Cys Lys Gly Glu Lys<br>210                    215                  220 | | 912 |
| aag ctg ttg cac ttc atc cag ctt gtc atc atg tgg aag aac agc ttg<br>Lys Leu Leu His Phe Ile Gln Leu Val Ile Met Trp Lys Asn Ser Leu<br>                  225                  230                235 | | 960 |
| ttt gag ttt gtg tct gag cac cgg ctc aac tgc ccc agg gag ctc ctt<br>Phe Glu Phe Val Ser Glu His Arg Leu Asn Cys Pro Arg Glu Leu Leu<br>240                    245                  250 | | 1008 |
| gct aaa gcc aaa gga gaa aac ctc ttt aag gat gaa aac tcg gtg gtg<br>Ala Lys Ala Lys Gly Glu Asn Leu Phe Lys Asp Glu Asn Ser Val Val<br>255                    260                  265                270 | | 1056 |
| tac ccc atc gtg gac ttc cct ctg cga gac atc tct ctt gcc tcc cag<br>Tyr Pro Ile Val Asp Phe Pro Leu Arg Asp Ile Ser Leu Ala Ser Gln<br>                  275                  280                285 | | 1104 |
| agg ggc att gca gag cac agc gct gcc ttg gcc tcc cgt gcc cgc gtc<br>Arg Gly Ile Ala Glu His Ser Ala Ala Leu Ala Ser Arg Ala Arg Val<br>                  290                  295                300 | | 1152 |
| ctg cag cag cgc cag acc att gag ctg atc ccc ctc aca gaa gtt cac<br>Leu Gln Gln Arg Gln Thr Ile Glu Leu Ile Pro Leu Thr Glu Val His<br>305                    310                  315 | | 1200 |
| tat tgg tac caa gga aag act tat gtc tac tac atc tat ggc act gac<br>Tyr Trp Tyr Gln Gly Lys Thr Tyr Val Tyr Tyr Ile Tyr Gly Thr Asp<br>320                    325                  330 | | 1248 |
| cac cag gtg tat gcg gtg gac tat cct gag cgg tat tgc tgt ggc tgt<br>His Gln Val Tyr Ala Val Asp Tyr Pro Glu Arg Tyr Cys Cys Gly Cys<br>335                    340                  345                350 | | 1296 |
| acc atc gtg tgacatagca tggctgtccc cagagcctgc cattcacgtt<br>Thr Ile Val | | 1345 |
| tgccaaggaa gatggccgac actctctgag tgtgttcact gttggctgca ttggacaatc | | 1405 |
| acatacaaac cctggcatgt ccttccagaa aaccagctt atcatctatc aagctccaac | | 1465 |
| cccttataca gctcctctgg tggaatccat gactcatatg tttaacctac aataattcag | | 1525 |
| ctatacccat tcctgtaaaa | | 1545 |

<210> SEQ ID NO 4
<211> LENGTH: 353
<212> TYPE: PRT
<213> ORGANISM: Homo sapiens

<400> SEQUENCE: 4

Met Pro Ser Pro Val Gly Leu Leu Arg Ala Leu Pro Leu Pro Trp Pro
1                  5                    10                  15

Gln Phe Leu Ala Cys Thr Leu Arg Arg Leu Ala Gly Pro Arg Glu Ser
                  20                  25                  30

Thr Gly Pro Ser Gln Lys Pro Pro Pro Leu Cys Ser Val Pro Cys Arg
                  35                  40                  45

Val Pro Ala Met Thr Glu Glu Val Ala Arg Glu Ala Leu Leu Ser Phe
        50                  55                  60

Val Asp Ser Lys Cys Cys Tyr Ser Ser Thr Val Ala Gly Asp Leu Val
65                  70                  75                  80

Ile Gln Glu Leu Lys Arg Gln Thr Leu Cys Arg Tyr Arg Leu Glu Thr

```
                85                  90                  95
Phe Ser Glu Ser Arg Ile Ser Glu Trp Thr Phe Gln Pro Phe Thr Asn
            100                 105                 110

His Ser Val Asp Gly Pro Gln Arg Gly Ala Ser Pro Arg Leu Trp Asp
        115                 120                 125

Ile Lys Val Gln Gly Pro Pro Met Phe Gln Glu Asp Thr Arg Lys Phe
    130                 135                 140

Gln Val Pro His Ser Ser Leu Val Lys Glu Cys His Lys Cys His Gly
145                 150                 155                 160

Arg Gly Arg Tyr Lys Cys Ser Gly Cys His Gly Ala Gly Thr Val Arg
                165                 170                 175

Cys Pro Ser Cys Cys Gly Ala Lys Arg Lys Ala Lys Gln Ser Arg Arg
            180                 185                 190

Cys Gln Leu Cys Ala Gly Ser Gly Arg Arg Cys Ser Thr Cys Ser
        195                 200                 205

Gly Arg Gly Asn Lys Thr Cys Ala Thr Cys Lys Gly Glu Lys Lys Leu
    210                 215                 220

Leu His Phe Ile Gln Leu Val Ile Met Trp Lys Asn Ser Leu Phe Glu
225                 230                 235                 240

Phe Val Ser Glu His Arg Leu Asn Cys Pro Arg Glu Leu Leu Ala Lys
                245                 250                 255

Ala Lys Gly Glu Asn Leu Phe Lys Asp Glu Asn Ser Val Val Tyr Pro
            260                 265                 270

Ile Val Asp Phe Pro Leu Arg Asp Ile Ser Leu Ala Ser Gln Arg Gly
        275                 280                 285

Ile Ala Glu His Ser Ala Ala Leu Ala Ser Arg Ala Arg Val Leu Gln
    290                 295                 300

Gln Arg Gln Thr Ile Glu Leu Ile Pro Leu Thr Glu Val His Tyr Trp
305                 310                 315                 320

Tyr Gln Gly Lys Thr Tyr Val Tyr Ile Tyr Gly Thr Asp His Gln
                325                 330                 335

Val Tyr Ala Val Asp Tyr Pro Glu Arg Tyr Cys Cys Gly Cys Thr Ile
            340                 345                 350

Val

<210> SEQ ID NO 5
<211> LENGTH: 1399
<212> TYPE: DNA
<213> ORGANISM: Homo sapiens
<220> FEATURE:
<221> NAME/KEY: CDS
<222> LOCATION: (254)...(1159)

<400> SEQUENCE: 5
ctcacactgg ctggcactgc taagcaggtg cggaggggag tcagagaccc ccggatggag      60 ggtgtggtg gacctcagtt ttgaggccga gagtcctctg gcgcccccca cagagctcct     120
ggagagactg cccagctatg actggcttct tcaaggggc agaggacaga tattcttccc     180
acctttggag gccccaggga ggccccagga gcaaaggtcc tggccctcgt tcctggaaca    240
cagagtccct gcg atg acg gag gag gtg gcc cgg gaa gcc ctc ctc agc       289
            Met Thr Glu Glu Val Ala Arg Glu Ala Leu Leu Ser
              1               5                  10 ttt gtg gac tct aag tgc tgc tac agc agc acg gtg gct gga gac ctc      337
Phe Val Asp Ser Lys Cys Cys Tyr Ser Ser Thr Val Ala Gly Asp Leu
        15                  20                  25
```

|  |  |
|---|---:|
| gtc atc cag gag ctg aag cgg cag acc ctc tgc agg tac cgt ctg gag<br>Val Ile Gln Glu Leu Lys Arg Gln Thr Leu Cys Arg Tyr Arg Leu Glu<br>    30                      35                    40 | 385 |
| acc ttt agt gaa tcc agg ata agc gag tgg aca ttt caa ccc ttt act<br>Thr Phe Ser Glu Ser Arg Ile Ser Glu Trp Thr Phe Gln Pro Phe Thr<br>45                    50                    55                  60 | 433 |
| aac cac tct gtg gat ggg ccg caa aga ggc gcc tcc ccc agg ctc tgg<br>Asn His Ser Val Asp Gly Pro Gln Arg Gly Ala Ser Pro Arg Leu Trp<br>                  65                    70                    75 | 481 |
| gac atc aag gtt caa ggt cct ccg atg ttt cag gaa gac acc agg aag<br>Asp Ile Lys Val Gln Gly Pro Pro Met Phe Gln Glu Asp Thr Arg Lys<br>80                    85                    90 | 529 |
| ttc cag gtc cct cac tcg tca ctg gtc aag gaa tgc cac aaa tgc cat<br>Phe Gln Val Pro His Ser Ser Leu Val Lys Glu Cys His Lys Cys His<br>          95                    100                 105 | 577 |
| ggg cgt ggg cgg tac aag tgc agc ggc tgc cac ggg gcg ggc acg gtg<br>Gly Arg Gly Arg Tyr Lys Cys Ser Gly Cys His Gly Ala Gly Thr Val<br>110                   115                 120 | 625 |
| cgg tgc cca tcc tgc tgc gga gcc aag cgc aaa gcc aag cag tcc cgg<br>Arg Cys Pro Ser Cys Cys Gly Ala Lys Arg Lys Ala Lys Gln Ser Arg<br>125                   130                 135                 140 | 673 |
| aga tgt cag ctg tgc gcg ggg tcc ggc agg cga aga tgc agc act tgc<br>Arg Cys Gln Leu Cys Ala Gly Ser Gly Arg Arg Arg Cys Ser Thr Cys<br>                  145                 150                 155 | 721 |
| tca ggg aga ggg aac aag acc tgc gcc acc tgc aag ggg gag aag aag<br>Ser Gly Arg Gly Asn Lys Thr Cys Ala Thr Cys Lys Gly Glu Lys Lys<br>160                   165                 170 | 769 |
| ctg ttg cac ttc atc cag ctt gtc atc atg tgg aag aac agc ttg ttt<br>Leu Leu His Phe Ile Gln Leu Val Ile Met Trp Lys Asn Ser Leu Phe<br>                  175                 180                 185 | 817 |
| gag ttt gtg tct gag cac cgg ctc aac tgc ccc agg gag ctc ctt gct<br>Glu Phe Val Ser Glu His Arg Leu Asn Cys Pro Arg Glu Leu Leu Ala<br>190                   195                 200 | 865 |
| aaa gcc aaa gga gaa aac ctc ttt aag gat gaa aac tcg gtg gtg tac<br>Lys Ala Lys Gly Glu Asn Leu Phe Lys Asp Glu Asn Ser Val Val Tyr<br>205                   210                 215                 220 | 913 |
| ccc atc gtg gac ttc cct ctg cga gac atc tct ctt gcc tcc cag agg<br>Pro Ile Val Asp Phe Pro Leu Arg Asp Ile Ser Leu Ala Ser Gln Arg<br>                  225                 230                 235 | 961 |
| ggc att gca gag cac agc gct gcc ttg gcc tcc cgt gcc cgc gtc ctg<br>Gly Ile Ala Glu His Ser Ala Ala Leu Ala Ser Arg Ala Arg Val Leu<br>240                   245                 250 | 1009 |
| cag cag cgc cag acc att gag ctg atc ccc ctc aca gaa gtt cac tat<br>Gln Gln Arg Gln Thr Ile Glu Leu Ile Pro Leu Thr Glu Val His Tyr<br>255                   260                 265 | 1057 |
| tgg tac caa gga aag act tat gtc tac tac atc tat ggc act gac cac<br>Trp Tyr Gln Gly Lys Thr Tyr Val Tyr Tyr Ile Tyr Gly Thr Asp His<br>                  270                 275                 280 | 1105 |
| cag gtg tat gcg gtg gac tat cct gag cgg tat tgc tgt ggc tgt acc<br>Gln Val Tyr Ala Val Asp Tyr Pro Glu Arg Tyr Cys Cys Gly Cys Thr<br>285                   290                 295                 300 | 1153 |
| atc gtg tgacatagca tggctgtccc cagagcctgc cattcacgtt tgccaaggaa<br>Ile Val | 1209 |
| gatggccgac actctctgag tgtgttcact gttggctgca ttggacaatc acatacaaac | 1269 |
| cctggcatgt ccttccagaa aaaccagctt atcatctatc aagctccaac ccttataca | 1329 |
| gctcctctgg tggaatccat gactcatatg tttaacctac aataattcag ctataccat | 1389 |
| tcctgtaaaa | 1399 |

<210> SEQ ID NO 6
<211> LENGTH: 302
<212> TYPE: PRT
<213> ORGANISM: Homo sapiens

<400> SEQUENCE: 6

Met Thr Glu Glu Val Ala Arg Glu Ala Leu Leu Ser Phe Val Asp Ser
 1               5                  10                  15

Lys Cys Cys Tyr Ser Ser Thr Val Ala Gly Asp Leu Val Ile Gln Glu
            20                  25                  30

Leu Lys Arg Gln Thr Leu Cys Arg Tyr Arg Leu Glu Thr Phe Ser Glu
        35                  40                  45

Ser Arg Ile Ser Glu Trp Thr Phe Gln Pro Phe Thr Asn His Ser Val
    50                  55                  60

Asp Gly Pro Gln Arg Gly Ala Ser Pro Arg Leu Trp Asp Ile Lys Val
65                  70                  75                  80

Gln Gly Pro Pro Met Phe Gln Glu Asp Thr Arg Lys Phe Gln Val Pro
                85                  90                  95

His Ser Ser Leu Val Lys Glu Cys His Lys Cys His Gly Arg Gly Arg
            100                 105                 110

Tyr Lys Cys Ser Gly Cys His Gly Ala Gly Thr Val Arg Cys Pro Ser
        115                 120                 125

Cys Cys Gly Ala Lys Arg Lys Ala Lys Gln Ser Arg Arg Cys Gln Leu
    130                 135                 140

Cys Ala Gly Ser Gly Arg Arg Cys Ser Thr Cys Ser Gly Arg Gly
145                 150                 155                 160

Asn Lys Thr Cys Ala Thr Cys Lys Gly Glu Lys Lys Leu Leu His Phe
                165                 170                 175

Ile Gln Leu Val Ile Met Trp Lys Asn Ser Leu Phe Glu Phe Val Ser
            180                 185                 190

Glu His Arg Leu Asn Cys Pro Arg Glu Leu Leu Ala Lys Ala Lys Gly
        195                 200                 205

Glu Asn Leu Phe Lys Asp Glu Asn Ser Val Val Tyr Pro Ile Val Asp
    210                 215                 220

Phe Pro Leu Arg Asp Ile Ser Leu Ala Ser Gln Arg Gly Ile Ala Glu
225                 230                 235                 240

His Ser Ala Ala Leu Ala Ser Arg Ala Arg Val Leu Gln Gln Arg Gln
                245                 250                 255

Thr Ile Glu Leu Ile Pro Leu Thr Glu Val His Tyr Trp Tyr Gln Gly
            260                 265                 270

Lys Thr Tyr Val Tyr Tyr Ile Tyr Gly Thr Asp His Gln Val Tyr Ala
        275                 280                 285

Val Asp Tyr Pro Glu Arg Tyr Cys Cys Gly Cys Thr Ile Val
    290                 295                 300

<210> SEQ ID NO 7
<211> LENGTH: 44
<212> TYPE: DNA
<213> ORGANISM: Artificial Sequence
<220> FEATURE:
<223> OTHER INFORMATION: Artificially synthesized adapter sequence

<400> SEQUENCE: 7
ctaatacgac tcactatagg gctcgagcgg ccgcccgggc aggt                    44

<210> SEQ ID NO 8

```
<211> LENGTH: 10
<212> TYPE: DNA
<213> ORGANISM: Artificial Sequence
<220> FEATURE:
<223> OTHER INFORMATION: Artificially synthesized adapter sequence

<400> SEQUENCE: 8
acctgcccgg                                                               10

<210> SEQ ID NO 9
<211> LENGTH: 43
<212> TYPE: DNA
<213> ORGANISM: Artificial Sequence
<220> FEATURE:
<223> OTHER INFORMATION: Artificially synthesized adapter sequence

<400> SEQUENCE: 9
tgtagcgtga agacgacaga aagggcgtgg tgcggagggc ggt                          43

<210> SEQ ID NO 10
<211> LENGTH: 11
<212> TYPE: DNA
<213> ORGANISM: Artificial Sequence
<220> FEATURE:
<223> OTHER INFORMATION: Artificially synthesized adapter sequence

<400> SEQUENCE: 10
accgccctcc g                                                             11

<210> SEQ ID NO 11
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 11
ctaatacgac tcactatagg gc                                                 22

<210> SEQ ID NO 12
<211> LENGTH: 21
<212> TYPE: DNA
<213> ORGANISM: Artificial Sequence
<220> FEATURE:
<223> OTHER INFORMATION: Artificially synthesized primer sequence

<400> SEQUENCE: 12
tgtagcgtga agacgacaga a                                                  21

<210> SEQ ID NO 13
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 13
tcgagcggcc gcccgggcag gt                                                 22

<210> SEQ ID NO 14
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 14
```

-continued

```
agggcgtggt gcggagggcg gt                                              22

<210> SEQ ID NO 15
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 15
ccagggtttt cccagtcacg ac                                              22

<210> SEQ ID NO 16
<211> LENGTH: 22
<212> TYPE: DNA
<213> ORGANISM: Artificial Sequence
<220> FEATURE:
<223> OTHER INFORMATION: Artificially synthesized primer sequence

<400> SEQUENCE: 16
tcacacagga aacagctatg ac                                              22

<210> SEQ ID NO 17
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 17
gatgctttcg tagttcagat gtaa                                            24

<210> SEQ ID NO 18
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 18
aatgcagcaa gaggtggtgg agat                                            24

<210> SEQ ID NO 19
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 19 gaggggatc agctcaatgg tctg                                             24

<210> SEQ ID NO 20
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 20
accccatcgt ggacttccct ctgc                                            24

<210> SEQ ID NO 21
<211> LENGTH: 24
<212> TYPE: DNA
```

```
<213> ORGANISM: Artificial Sequence
<220> FEATURE:
<223> OTHER INFORMATION: Artificially synthesized primer sequence

<400> SEQUENCE: 21
tcatcatctc tgcccctct gctg                                               24

<210> SEQ ID NO 22
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 22
gacgcctgct tcaccacctt cttg                                              24

<210> SEQ ID NO 23
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 23
ctggtgcagt tggtgaggtt ttct                                              24

<210> SEQ ID NO 24
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 24
caatcaccgt ccccaagtca ccag                                              24

<210> SEQ ID NO 25
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 25
agtcgcggcc gccggtatgc agagaagagg acagaa                                 36

<210> SEQ ID NO 26
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 26
agtcgcggcc gcaaaagggg tgaaagagaa gattgc                                 36

<210> SEQ ID NO 27
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 27
cttttgagca agttcagcct                                                   20
```

```
<210> SEQ ID NO 28
<211> LENGTH: 24
<212> TYPE: DNA
<213> ORGANISM: Artificial Sequence
<220> FEATURE:
<223> OTHER INFORMATION: Artificially synthesized primer sequence

<400> SEQUENCE: 28
ttgaaatgtc cactcgctta tcct                                          24

<210> SEQ ID NO 29
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 29
agtcgcggcc gcgctaagca ggtgcggagg ggagtc                             36

<210> SEQ ID NO 30
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 30
agtcgcggcc gccagatatt cttcccacct ttggag                             36

<210> SEQ ID NO 31
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 31
agtcgcggcc gcgaggagct gtataagggg ttggag                             36

<210> SEQ ID NO 32
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 32
agtcgcggcc gctgccaggg tttgtatgtg attgtc                             36

<210> SEQ ID NO 33
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2, 3, 5, 7
<223> OTHER INFORMATION: Xaa = any amino acid

<400> SEQUENCE: 33

Cys Xaa Xaa Cys Xaa Gly Xaa Gly
 1               5
```

```
<210> SEQ ID NO 34
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2, 3, 5
<223> OTHER INFORMATION: Xaa = any amino acid

<400> SEQUENCE: 34

Cys Xaa Xaa Cys Xaa Gly
 1               5

<210> SEQ ID NO 35
<211> LENGTH: 8
<212> TYPE: PRT
<213> ORGANISM: Artificial Sequence
<220> FEATURE:
<223> OTHER INFORMATION: binding consensus sequence
<220> FEATURE:
<221> NAME/KEY: VARIANT
<222> LOCATION: 1
<223> OTHER INFORMATION: Xaa = Ala or Gly
<220> FEATURE:
<221> NAME/KEY: VARIANT
<222> LOCATION: 2, 3, 4, 5
<223> OTHER INFORMATION: Xaa = any amino acid residue
<220> FEATURE:
<221> NAME/KEY: VARIANT
<222> LOCATION: 8
<223> OTHER INFORMATION: Xaa = Ser or Thr

<400> SEQUENCE: 35

Xaa Xaa Xaa Xaa Xaa Gly Lys Xaa
 1               5

<210> SEQ ID NO 36
<211> LENGTH: 4
<212> TYPE: PRT
<213> ORGANISM: Artificial Sequence
<220> FEATURE:
<223> OTHER INFORMATION: 4-mer peptide
<220> FEATURE:
<221> NAME/KEY: VARIANT
<222> LOCATION: 2 and 3
<223> OTHER INFORMATION: Xaa = alphatic amino acid
<220> FEATURE:
<221> NAME/KEY: VARIANT
<222> LOCATION: 4
<223> OTHER INFORMATION: Xaa = any amino acid

<400> SEQUENCE: 36

Cys Xaa Xaa Xaa
 1
```